US006288029B1

(12) United States Patent
Mutter et al.

(10) Patent No.: US 6,288,029 B1
(45) Date of Patent: Sep. 11, 2001

(54) TEMPLATE ASSOCIATED NPY Y2-RECEPTOR AGONISTS

(76) Inventors: Manfred Mutter, Chemin de la Venoge 9, 1028 Préverenges Vaud; Jean-Silvain Lacroix, Chemin des Campanules 1, 1219 Aïre Geneva; Eric Grouzmann, Chemin du Creux-de-Corsy 57, 1093 La Conversion Vaud, all of (CH)

( * ) Notice: Subject to any disclaimer, the term of this patent is extended or adjusted under 35 U.S.C. 154(b) by 0 days.

(21) Appl. No.: 09/229,900

(22) Filed: Jan. 14, 1999

Related U.S. Application Data

(62) Division of application No. 09/054,393, filed on Apr. 3, 1998, now Pat. No. 6,017,879.
(51) Int. Cl.$^7$ ............................. A61K 38/12; A61K 38/16
(52) U.S. Cl. .................................. 514/9; 514/11; 514/12; 514/15
(58) Field of Search .................................. 514/9, 11, 12, 514/15

(56) References Cited

U.S. PATENT DOCUMENTS 5,696,093   12/1997   Tseng, et al. .
6,017,879 *  1/2000   Mutter et al. ............................ 514/11

OTHER PUBLICATIONS

Baraniuk et al. J. Appl. Physiol. (1992), 73(5), 1867–72, May 1992.*
Lacroix et al. J. Allergy Clin. Immunol. (1996), 98(3), 611–616, Mar. 1996.*
Lacroix et al. Br. J. Pharmacol. (1996), 118(8), 2074–2084, Aug. 1996.*
McLean et al. J. Allergy Clin. Immunol. 59(2), 165–170, Feb. 1977.*
Corren et al. Current Opinion in Pulmonary Medicine, (1999 Jan) 5 (1) 35–7, May 1992.*
Grouzmann et al. J. Biol. Chem., 272(12), 7699–7706, Mar. 1997.*
Baraniuk, et al., "Neuropeptide Y (NPY) in Human Nasal Mucosa," *Am. J. Respir. Cell. Mol. Biol.* 3:165–173 (1990).
Baraniuk, et al., "Neuropeptide Y is a Vasoconstrictor in Human Nasal Mucosa," *J. Applied Physiol.* 73:1867–1872 (1992).
Beck–Sickinger, et al., "Complete L–Alanine Scan of Neuropeptide Y Reveals Ligands Binding to $Y_1$ and $Y_2$ Receptors With Distinguished Conformations," *Eur. J. Biochem.* 225:947–958 (1994).
Dumy, et al., "A Convenient Synthesis of Cyclic Peptides as Regioselectively Addressable Functionalized Templates (RAFT)," *Tetrahedron Letters* 36:1255–1258 (1995).
Ekblad, et al., "Neuropeptide Y Co–exists and Co–operates With Noradrenaline in Perivascular Nerve Fibers," *Regulatory Peptides* 8:225–235 (1984).
Ernest, et al., "Three Novel Mimics for the Construction of Sterically Constrained Protein Turn Models," *Tetrahedron Letters* 31:4011–4014 (1990).
Ernest, et al., "Cyclic Templates With Incorporated Turn–Inducing Mimics," *Helvetica Chimica Acta* 76:1539–1563 (1993).
Futaki, et al., "Preparation of Peptide Thioesters Using Fmoc–Solid–Phase Peptide Synthesis and Its Application to the Construction of a Template–Assembled Synthetic Protein (TASP)," *Tetrahedron Letters* 38:6237–6240 (1997).
Grouzmann, et al., "A Specific Template–Assembled Peptidic Agonist for the Angiotensin II Receptor Subtype 2 (AT2) and Its Effect on Inferior Olivary Neurones," *Eur. J. Biochem.* 234:44–49 (1995).
Grouzmann, et al., "Characterization of a Selective Antagonist Neuropeptide Y at the Y2 Receptor," *J. Biol. Chem.* 272:7699–7706 (1997).
Grove, et al., "Template–Assembled Synthetic Proteins Designed to Adopt a Globular, Four–Helix Bundle Conformation Form Ionic Channels in Lipid Bilayers," *J. Am. Chem. Soc.* 115:5919–5924 (1993).
LaCroix, et al., "Intranasal Administration of Neuropeptide Y in Man: Systemic Absorption and Functional Effects," *Brit. J. Pharmacol.* 118:2079–2084 (1996).
LaCroix, et al., "Attenuation of Allergen–Evoked Nasal Responses by Local Pretreatment With Exogenous Neuropeptide Y in Atopic Patients," *J. Allergy Clin. Immunol.* 98:611–616 (1996).
LaCroix, et al., "Post–Exercise Nasal Vasoconstriction and Hyporeactivity: Possible Involvement of Neuropeptide Y," *Acta Otolaryngol (Stockh.)* 117:000–000 (1997).
Michel, "Receptors for Neuropeptide Y: Multiple Subtypes and Multiple Second Messengers," *Trends in Parmacol. Sci.* 12:389–394 (1991).
Minth, et al., "Cloning, Characterization, and DNA Sequence of a Human cDNA Encoding Neuropeptide Tyrosine," *Proc. Natl. Acad. Sci. USA* 81:4577–4581 (1984).
Mutter et al., "Artificial Folding Units of Assembly of Amphiphilic Secondary Structures on a Template," *Helvetica Chimica Acta* 71:835–847 (1988).
Mutter, "Nature's Rules and Chemist's Tools: A Way for Creating Novel Proteins," *Trends in Biochem. Sci.* 13:260–265 (1988).

(List continued on next page.)

*Primary Examiner*—Michael Borin

(57) ABSTRACT

The present invention is directed to agonists of neuropeptide Y (NPY) or PYY that are formed by combining these peptides or a portion of these peptides with a template that promotes biologically active folds. Typically, templates consist of cyclized peptides containing one or more naphthyl ring structures. The agonists may be used in the treatment of diseases and conditions known to be responsive to NPY or PYY and, particularly in the treatment of asthma, rhinitis, and bronchitis.

15 Claims, 11 Drawing Sheets

OTHER PUBLICATIONS

Mutter, et al., "A Chemical Approach to Protein Design–Template–Assembled Synthetic Proteins (TASP)," *Angewandte Chemie* 28:535–676 (1989).

Mutter, et al., "Template–Assembled Synthetic Proteins With Four–Helix–Bundle Topology. Total Chemical Synthesis and Conformational Studies," *J. Am. Chem. Soc.* 114:1463–1470 (1992).

Mutter, et al., "Non–Native Architectures in Protein Design and Mimicry," *CMLS, Cell. Mol. Life. Sci.* 53:851–863 (1997).

Nyanguile, et al., "Synthesis of Antiparallel 4α–Helix Bundle TASP by Chemoselective Ligation," *Letters in Peptide Sci.* 1:9–16 (1994).

Rist, et al., "Modified, Cyclic Dodecapeptide Analog of Neuropeptide Y is the Smallest Full Agonist at the Human $Y_2$ Receptor," *FEBS Letters* 394:169–173 (1996).

Sahu, et al., "Neuropeptidergic Regulation of Feeding Behavior, Neuropeptide Y," *Trends in Endocrinology & Metabolism* 4:217–224 (1993).

Sila, et al., "Topological Templates as Tool in Molecular Recognition and Peptide Mimicry: Synthesis of a TASK Library," *J. Mol. Recog.* 8:29–34 (1995).

Stanley, et al., "Neuropeptide Y Injected in the Paraventricular Hypothalamus: A Powerful Stimulant of Feeding Behavior," *Proc. Natl. Acad. Sci. USA* 82:3940–2943 (1985).

Tuchscherer, et al., "Total Chemical Synthesis, Characterization, and Immunological Properties of an MHC Class I Model Using the TASP Concept for Protein *de novo* Design," *Protein Science* 1:1377–1386 (1992).

Tuchscherer, et al., "Designing Novel Proteins," *Chemistry & Industry* 4:597–601 (1997).

Wahlestedt, et al., "Neuropeptide Y–Related Peptides and Their Receptors–Are the Receptors Potential Therapeutic Drug Targets?," *Ann. Rev. Pharmacol. Toxicol.* 32:309–352 (1993).

Walker, et al., "The Role of Neuropeptide Y in Cardiovascular Regulation," *Trends in Pharmacol. Sci.* 12:111–115 (1991).

\* cited by examiner

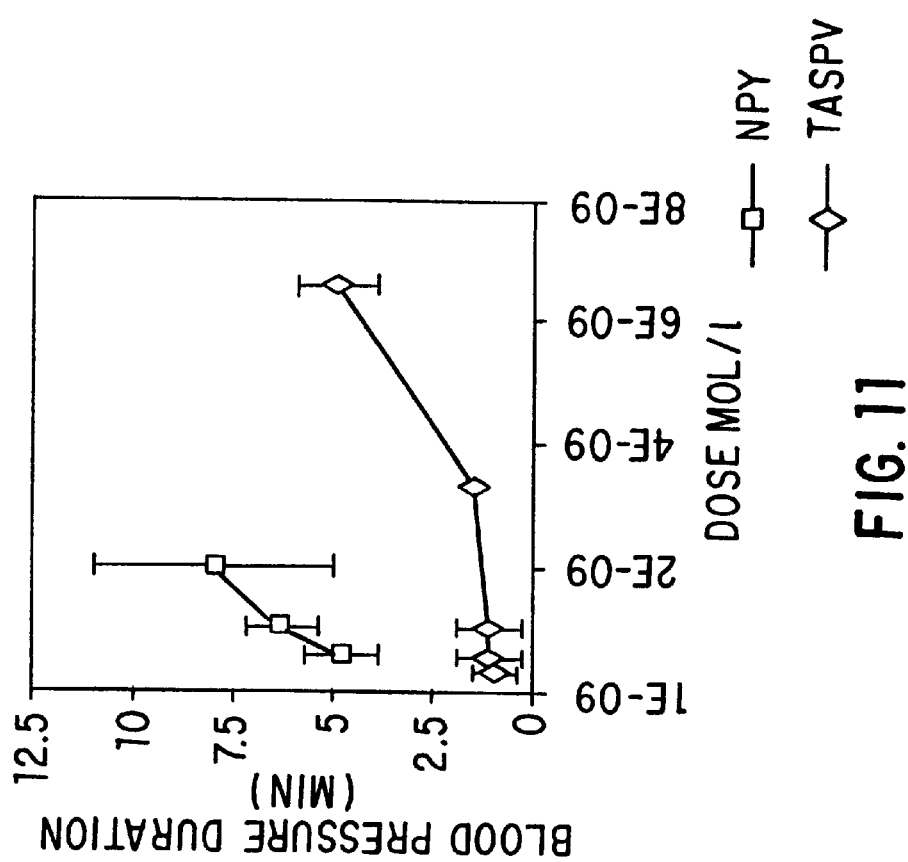
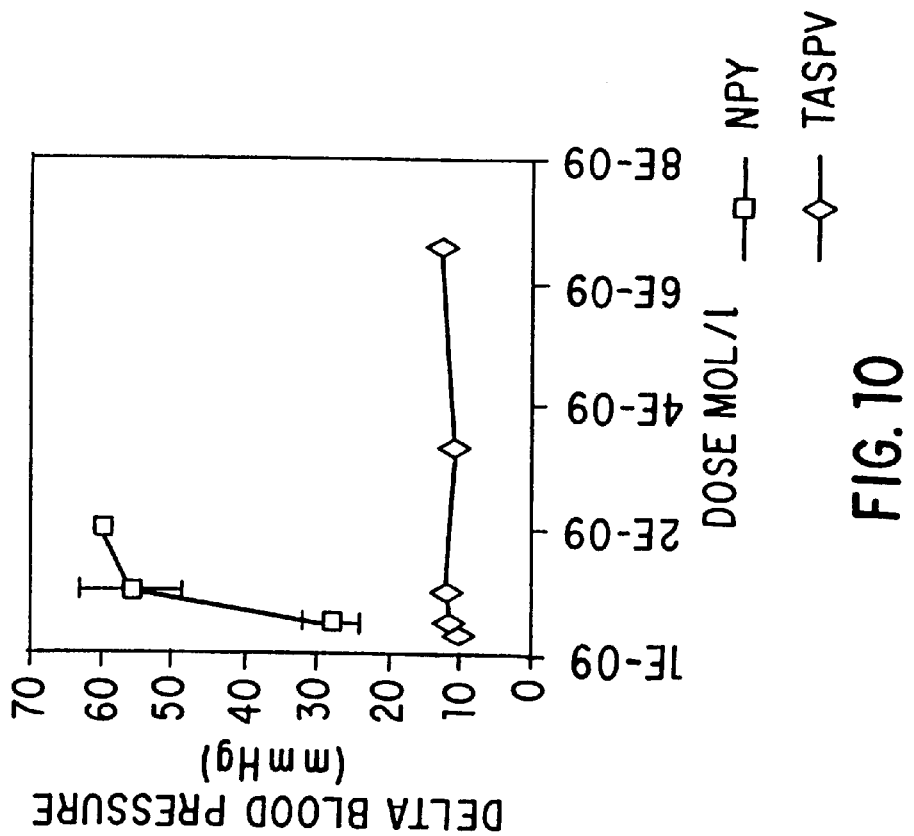

TEMPLATE ASSOCIATED NPY Y2-RECEPTOR AGONISTS

CROSS REFERENCE TO RELATED APPLICATION

The present application is a division of U.S. application Ser. No. 09/054,393, filed Apr. 3, 1998 (now U.S. Pat. No. 6,017,879).

FIELD OF THE INVENTION

The present invention is directed to a new type of agonist that interacts preferentially with the neuropeptide Y (NPY) Y2 receptor. The agonist contains one or more peptides with sequences from the C-terminal end of neuropeptide Y (NPY) or peptide YY (PYY) bound to a template that promotes the correct folding of these peptides. In addition, the present invention is directed to methods for reducing airway resistance in bronchial patients by administering NPY, PYY, or agonists of these peptides.

BACKGROUND OF THE INVENTION

Neuropeptide Y (NPY) is an amidated peptide widely distributed in the central and peripheral nervous systems (Tatemoto, et al., *Nature* 296:659–660 (1982); Ekblad, et al., *Regul. Peptides* 8:225–235 (1984)). It is present in all sympathetic nerves innervating the cardiovascular system and is the most abundant peptide in the brain and the heart (Tatemoto, et al., *Nature* 296:659–660 (1982)). In addition, NPY is present in platelets (Ericsson, et al., *Proc. Natl. Acad. Sci. U.S.A.* 84:5587–5591 (1987)), the endothelium (Id.); the adrenal medulla (Allen, et al., *J. Auton. Nerv. Sys.* 9:559–566 (1983)); the pancreas (Jamal, et al., *Endocrinology* 129:3372–3380 (1991)); the kidney (Grouzmann, et al., *Peptides* 15 (8):1377–1382 (1994)); and the pituitary gland (Gehlert, et al., *Peptides* 15 (4):651–656 (1994)). Peptide YY (PYY) is a closely related peptide that has similar biological effects to NPY and which is found primarily in the gut.

The biological actions of NPY and peptide YY are mediated by a number of G-protein coupled receptors termed Y1, Y2, Y3, Y4/PP and Y5 (Herzog, et al., *Proc. Natl. Acad. Sci. U.S.A.* 89:5794–5798 (1992)). Of these, the physiological effects associated with the Y1 and Y2 receptors are the best characterized. Exposure to a Y1 agonist causes an increase in blood pressure and potentiates post-synaptically the action of other vasoactive substances (Wahlestedt, et al., *J. Pharmacol. Exp. Ther.* 234:735–741 (1985)). In contrast, Y2 receptors are mainly located presynaptically and, upon stimulation, mediate the inhibition of neurotransmitter release (Westfall, et al., *J. Cardiovasc. Pharmacol.* 10:716–722 (1987)).

NPY has a number of biological effects of potential therapeutic importance. Intranasal administration of NPY reduces nasal airway resistance and vascular permeability without affecting submucosal gland secretion (Baraniuk, et al., *Am. J. Respir. Cell. Mol. Biol.* 3:165–173 (1990); Baraniuk, et al., *J. Appl. Physiol.* 73 (5):1867–72 (1992)). In healthy volunteers, intranasal pretreatment with exogenous NPY markedly reduces vasodilation and nasal secretion induced by afferent nerve stimulation with capsaicin or histamine (Lacroix, et al., Br. *J Pharmacol.* 118:2079–2084 (1996)). Therapeutic application of NPY in the treatment of rhinitis has been recently suggested since allergen-evoked nasal responses in patients are significantly attenuated after local pretreatment with the peptide (Lacroix, et al., *J. Allergy Clin. Immunol.* 98:611–616 (1996)).

NPY also plays an important role in modulating the cardiovascular system, behavior, anxiety and the secretion of certain hormones (Wahlestedt, et al., *Annu. Rev. Pharmacol. Toxicol.* 33:309–352 (1993); Michel, *Trends Pharmacol. Sci.* 12:389–394 (1991)). It contributes to the central and peripheral control of blood pressure, the regulation of feeding behavior, obesity, diabetes and psychiatric disorders (Walker, et al., *Trends Pharmacol Sci* 12:111–115 (1991); Sahu, et al., *Trends Endocrinol. Metab.* 4:217–224 (1993); Stanley, et al., *Proc. Natl. Acad. Sci. USA* 82:3940–3943 (1985)).

B. Structure of NPY and PYY

NPY is derived from the 97 amino acid precursor shown as SEQ ID NO:1 (Minth, et al., *Proc. Natl. Acad. Sci. USA* 81:4577–4581 (1984)). Amino acids 29–64 represent the 36 amino acid sequence which undergoes processing resulting in the addition of an N-terminal glycine and the amidation of the C-terminal tyrosine. The complete NPY sequence is needed for binding to the Y1 receptor, whereas C-terminal fragments are selective for the Y2 receptor (Ekblad, et al., *Regul. Peptides* 8:225–235 (1984)). The C-terminal pentapeptide amide is important for both receptors and probably represents the binding site (Beck-Sickinger, et al., *Eur. J. Biochem.* 225:947–958 (1994)). However, Arg33 and Arg35 may not be exchanged by L-alanine in the Y1 system, whereas Arg35 and Tyr36 are the most critical residues for the Y2 receptor. NPY fragments shorter than NPY 27–36 are no longer able to bind to the Y2 receptor.

Peptide YY also binds to the Y2 receptor. It is 36 amino acids in length and shares a 70% sequence homology with NPY. Its sequence is shown as SEQ ID NO:2.

C. Template Assembled Synthetic Proteins or Peptides (TASP)

In order to bypass the folding problem that has typically been associated with peptide and protein synthesis, a conceptually different approach to de novo protein design has recently been taken, the synthesis of template-assembled synthetic proteins or peptides (TASP). In this approach, topological templates direct covalently attached peptide blocks to a predetermined three-dimensional packing arrangement (FIGS. 1–3), thereby modifying their biological and pharmacokinetic properties ((Mutter, et al., *Helv. Chim. Acta,* 71:835–47 (1988); Mutter, *Trends Biochem. Sci.,* 13:260–5 (1988); Mutter, et al., *J. Am. Chem. Soc.* 114:1463–1470 (1992); Grouzmann, et al., *Eur. J. Biochem.* 234:44–49 (1995)). Typically, templates are constrained peptides, cyclodextrines or polycyclic systems.

Recently, the TASP concept was used to design a compound that selectively antagonizes the action of NPY at the Y2 receptor. A cyclic peptide exhibiting four attachment sites and a naphthyl derivative was used as template and NPY33–36 segments were attached by means of an oxime bond (Grouztnann, et al.,*J. Biol. Chem.* 292 (12):7699–7706 (1997)). This TASP molecule was investigated for binding to NPY Y1 and Y2 receptors and its antagonistic activity was established by its ability to prevent the NPY-induced increase in intracellular calcium.

D. TASP Agonists of NPY Y2 Receptor Interaction

It has now been discovered that template assembled synthetic peptides can produce NPY and PYY agonists that interact specifically with the Y2 receptor. These compounds may be used in the treatment of several conditions, including rhinitis. In addition, it has been discovered that NPY, PYY and agonists of these peptides may be used in treating bronchial diseases and related conditions.

SUMMARY OF THE INVENTION

The present invention is based upon two main discoveries. The first is that template assembled synthetic peptides can be produced that are agonists of NPY and PYY. These agonists can be used to effectively treat rhinitis and a variety of other physiological conditions. The second discovery is that NPY, PYY and their agonists reduce bronchial airway resistance. Thus, these agents may be used in treating bronchitis, asthma and related conditions.

In its first aspect, the present invention is directed to an agonist of NPY comprising a template and one or more peptides derived from NPY or PYY covalently bound to the template. The template is a cyclized peptide between 3 and 10 amino acids in length containing at least two residues that are joined by a naphthyl ring. At least one, and preferably two, linear peptides between 12 and 27 amino acids in length are covalently bound to the template, e.g., by an oxime bond. The C-terminal sequence of the bound peptide(s) has either the sequence: RHYINLITRQRY, (SEQ ID NO:3); or the sequence RHYLNLVTRQRY (SEQ ID NO:4). In either case, the C-terminal tyrosine should be amidated. In a preferred embodiment, linear peptides are attached at the lysine residues of the following template:

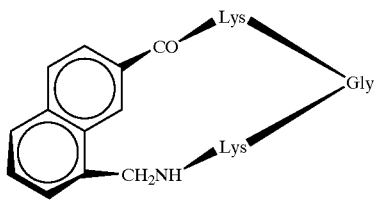

The 12 amino acid C-terminal sequences shown above may be preceded by additional portions of the NPY sequence, up to the full additional 24 amino acids found in NPY: YPSKPDNPGEDAPAEDMARYYSAL, (SEQ ID NO:5). For example, SEQ ID NO:3 may be preceded at its N-terminal end by NPY1-24; NPY2-24; NPY3-24 etc. It is expected that conservative changes in this 24 amino acid sequence can be made without affecting activity and, in particular, the "M" at position 17 can be effectively replaced with L. If agonists specific for the Y2 receptor are desired, then the full length NPY peptide should not be used. The most preferred peptide for attachment to the template has the sequence: YSALRHYINLITRQRY, (SEQ ID NO:6). The peptides may be preceded at their N-terminal end by a single aminooxy acetylated glycine. Although these peptides may be joined to templates by other covalent bonds, oxime bonds are generally preferred. The most preferred structure is that of TASP-V as follows:

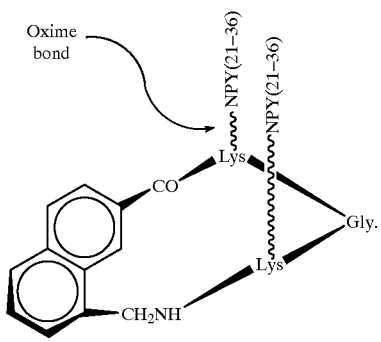

As an alternative, the linear peptides attached to the TASP template may be preceded by additional portions of the PYY sequence up to the fill additional 24 amino acids: YPIK-PEAPGEDASPEELNRYYASL (SEQ ID NO:7). In all cases, additions should be made so as to maintain the correct sequence order of PYY. The most preferred PYY fragment for attachment to templates is: YASLRHYLNLVTRQRY (SEQ ID NO:8). The attached peptides may be preceded at their N-terminal end by an aminooxy acetyl glycine and they are preferably bound to the template by an oxime bond. When the PYY fragment of SEQ ID NO:8 is used in place of the NPY fragments in TASP-V, a second preferred agonist is produced. In order to distinguish this second agonist from TASP-V, it is designated as TASP-V2.

All of the peptide agonists described above may be incorporated into a pharmaceutical composition and administered to a patient for the purpose of treating diseases or conditions that respond to NPY or PYY. In general, the agonists should be administered to patients in a dosage range of about 1 to 100 μg. Any route of delivery is consistent with the present invention but non-oral routes will typically be used to avoid possible destruction of agents in the gut.

In another aspect, the present invention is directed to a method of reducing airway resistance in a patient suffering from a bronchial disease or condition by administering NPY, PYY, or an NPY or PYY agonist, preferably an agonist specific for the Y2 receptor. When either NPY or PYY is used in treatments, the amidated, full length form of the peptide should be used. When a Y2 agonist is used, it should be a peptide containing, at a minimum, the sequence of amino acids 25–36 of NPY or PYY but not the full 36 amino acids. The most preferred agonists are TASP-V and TASP-V2.

Bronchial conditions or diseases are preferably treated by administering therapeutic agent in a pharmaceutical composition delivered by inhalation. A unit dose should provide a patient with between about 1 and 100 μg of active agent. Among the bronchial diseases and conditions that may be treated using this procedure are asthma and bronchitis.

In another aspect, the invention is directed to an improvement in methods for treating diseases or conditions responsive to NPY or PYY. This is accomplished by administering any of the TASP-type agonists described above, preferably one specific for the Y2 receptor, at a unit dose of between 1 and 100 μg. By "TASP-type agonists" we mean agonists in which peptides are covalently bound to a template such as those described herein. The preferred template is that shown above and the linear peptide attached to this template should contain the sequence of amino acids 25–36 of NPY or PYY. The linear peptide may also contain any portion of the additional contiguous amino acids which make up the sequence of intact NPY or PYY. The most preferred agonists are, again, TASP-V and TASP-V2. The NPY or PYY agonist may be used as an antihistamine, to increase body weight, or to treat rhinitis, asthma or bronchitis. Other diseases and conditions that may be treated are laryngitis, mucovisidose, chronic rhinosinusitis, oedema, inflammation, anxiety, congestive heart failure, cardiomyopathy, coronary artery disease, diminished cardiac vagal activity, hypertension, Alzheimer's Disease, epilepsy, ischemia, angina, myocardial infarction and diseases characterized by decreased immune responsiveness such as AIDS.

BRIEF DESCRIPTION OF THE DRAWINGS

FIG. 10: Postjunctional activity of TASP-V measured in rat as the peak response following injection of the peptide (ΔBP)

FIG. 11: Postjunctional activity of TASP-V measured in rat as the duration of this response (BP duration)

DETAILED DESCRIPTION OF THE INVENTION

In the following description, reference will be made to various methodologies well known to those skilled in the art of chemistry and medicine. Such methodologies are described in standard reference works setting forth the general principles of these disciplines.

I. Synthesis of TASP NPY Y2 Agonists

A. Making of Template

Figure 4:
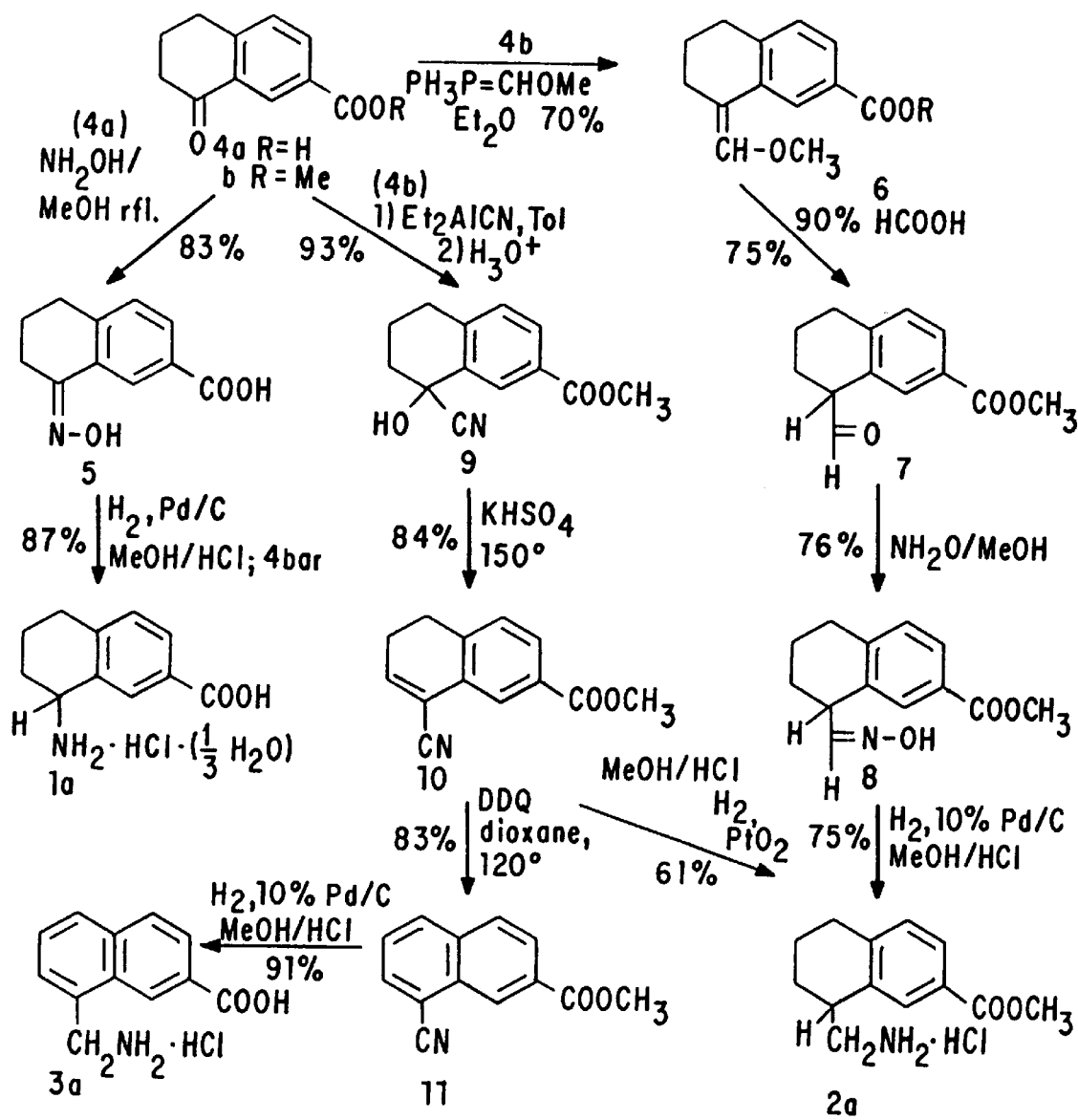
FIG. 4: Reactions leading to the production of turn mimics (1a, 2a and 3a) for incorporation into TASP templates (from Ernest et al., *Helv. Chim. Acta* 76:1539–1563 (1993), see page 1541).

The procedures used in the making of TASP templates in general, and, in particular, in making the template used in TASP-V, have been fully described in the literature (Ernest, et al., *Helv. Chim. Acta* 76:1539–1563; Ernest, et al., *Tetrahedron Lett.* 31:4011–4014 (1990)). The basic approach is to introduce an artificial turn-inducing mimic into a cyclized peptide chain so as to constrain it into a semi-rigid spatial arrangement. The three most commonly used turn mimics are: 8-amino-5,6,7,8-tetrahydronaphth-2-oic acid; 8-(aminomethyl)-5,6,7,8-tetrahydronaphth-2-oic acid; and 8-(aminomethyl)naphth-2-oic acid. Each of these may be synthesized from commercially available 4-phenylbutanoic acid. The basic reaction scheme used for producing each of these peptide mimics is shown in FIG. 4.

Prior to their incorporation into peptide chains, reactive groups in the turn mimics are transformed into their N-Boc and N-Fmoc derivatives. Free carboxyl groups on the blocked mimic are then reacted with the N-terminal amino acid in a peptide to form an amide bond. The C-terminal end of the peptide is reacted with deprotected NH groups on the mimic to form a cyclic structure. Many variations of these reactions may be performed depending upon the particular template desired. The peptides used in forming templates will typically be between 3 and 10 units long with the most preferred structure consisting of a glycine residue flanked at either end by one or two lysine amino acids. A typical template formed in this manner is shown as structure I in FIG. 5.

Figure 1:
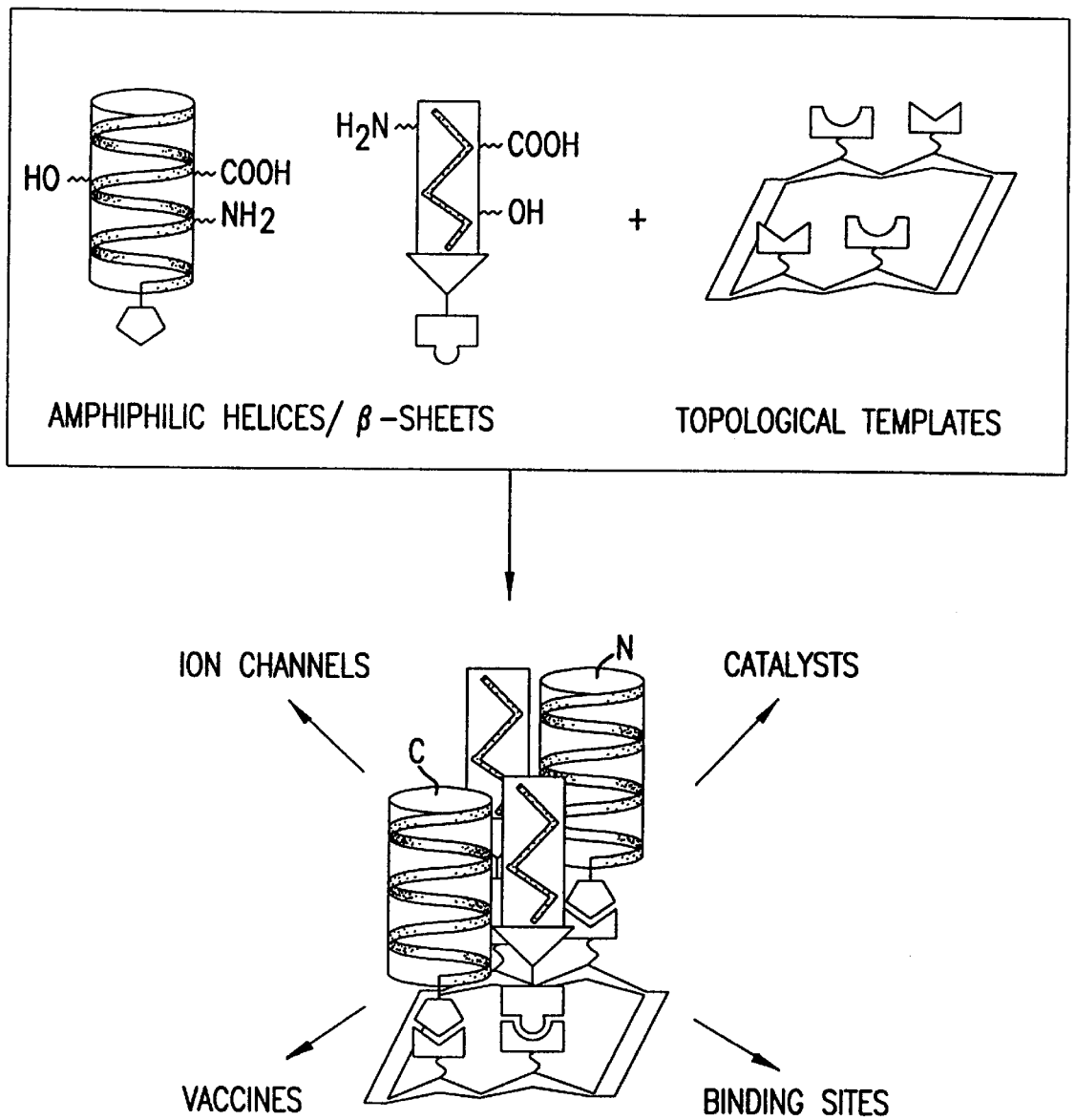
FIG. 1: The concept of template-assembled synthetic proteins (TASP) for the construction of functional protein mimetics. Topological templates (e.g. cyclic peptides, see FIG. 2) induce folding or spatial rearrangement of covalently attached peptide blocks (e.g. fragments of bioactive compounds) into predetermined packing arrangements. The enforced spatial proximity as well as the induction of specific conformations of the template assembled peptides may result in enhanced bioactivity and specificity and alter the pharmacokinetics in a characteristic way. The symbols denote chemoselectively reactive groups as outlined in FIG. 3.
Figure 2:
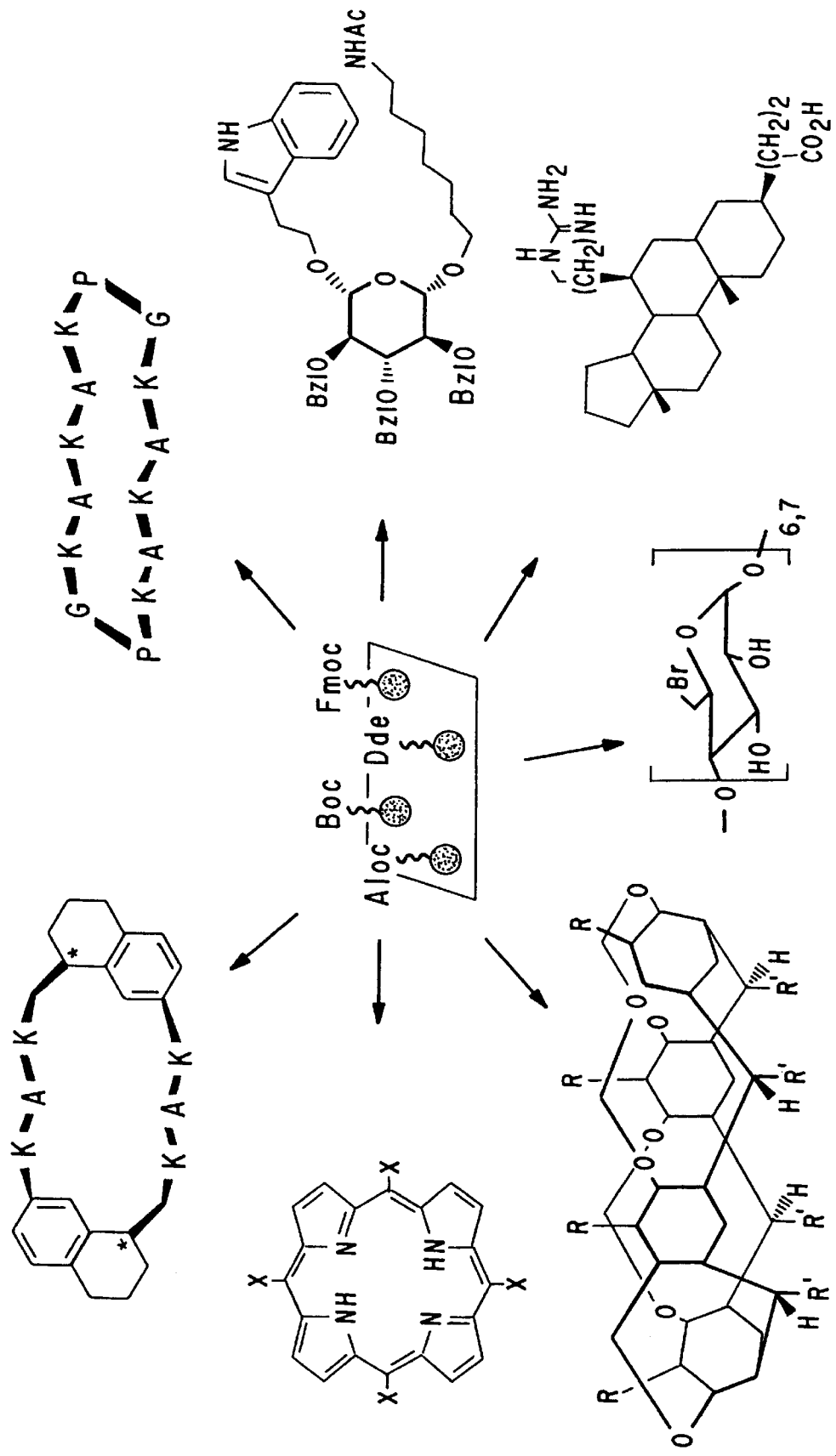
FIG. 2: A variety of molecules may serve as templates, e.g. cyclic peptides, monosaccharides, steroids, cyclodextrins, calixarenes or porphyrins. The structural requirement is an appropriate spatial orientation of selectively addressable attachment sites, e.g. orthogonally protected amino groups as schematically shown (center).
Figure 3:
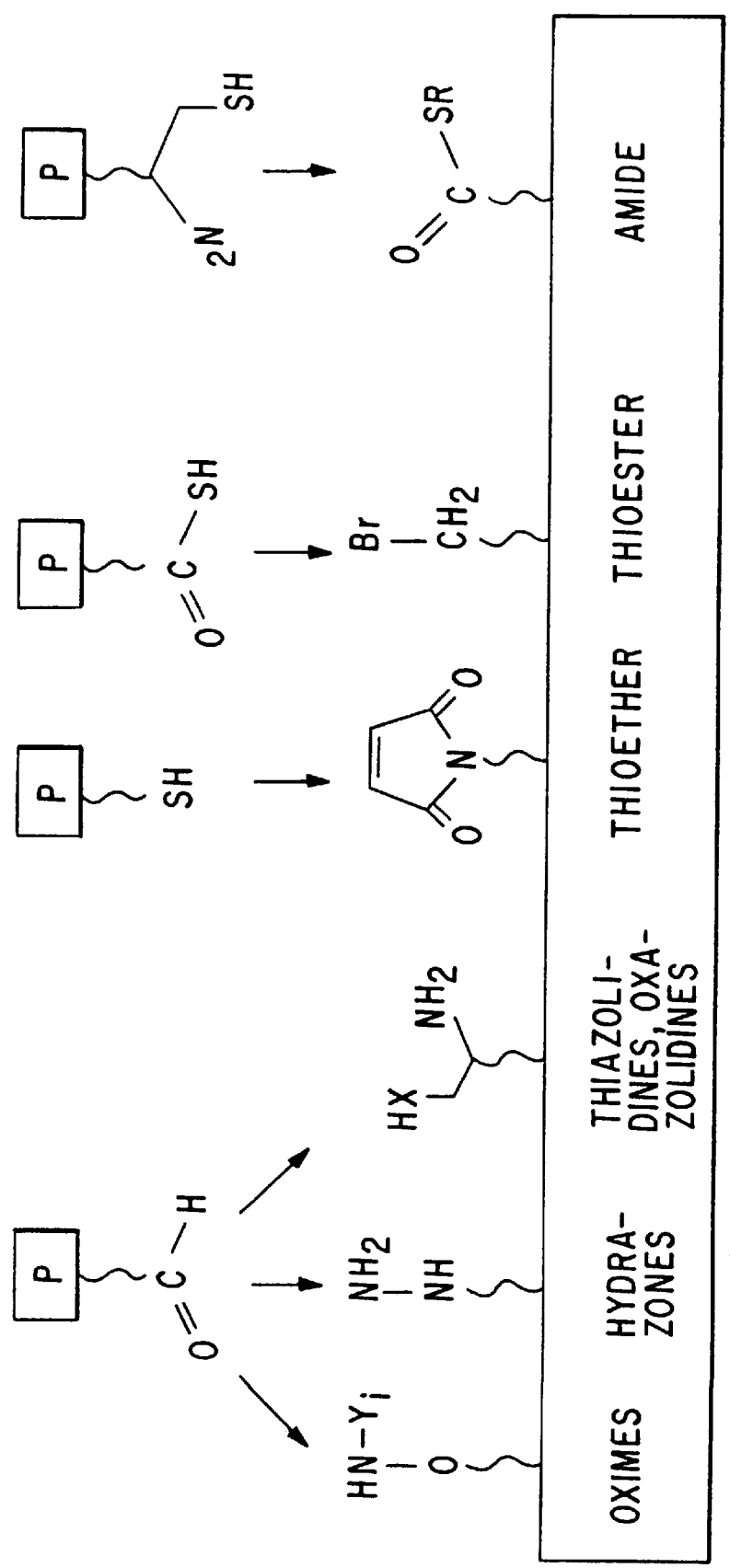
FIG. 3: Recently introduced chemoselective ligation methods allow for the condensation of completely unprotected peptide fragments (P) to correspondingly functionalized templates in aqueous solution.
Figure 5:
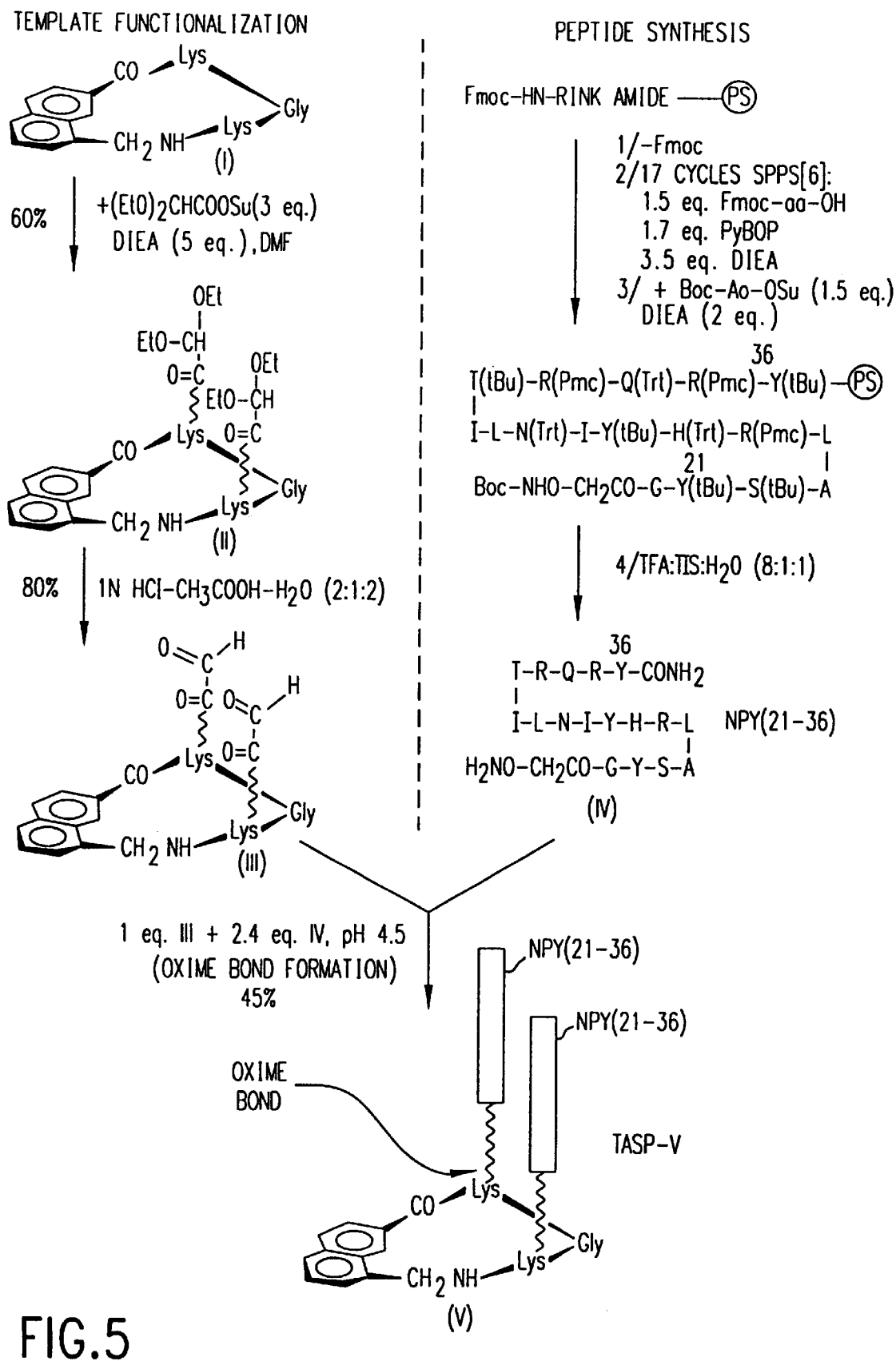
FIG. 5: Synthesis of TASP-V. Abbreviations: Lys=lysine; Gly=glycine; DIEA=diisopropylethylamine; oxime-bond= template-Lys (—N—CO—CH=NO—CH$_2$CO-peptide; Fmoc=fluorenylmethoxycarbonyl; PyBOP=benzotriazole-1-yl-oxy-tris-pyrrolidino-phosphonium hexafluorophosphate; Boc-AO-OSu=t-butyloxycarbonyl-aminooxyacetyl-N-hydroxy succinic ester; T=threonine; R=arginine; Q=glutamine; Y=tyrosine; Pmc=pentamethyl chroman sulphonyl; G=glycine; L=leucine; N=asparagine; H=histidine; I=isoleucine; S=serine; A=alanine.

Reactive side chain groups of the amino acids in the cyclized template form the site of attachment for one or more linear peptides derived from NPY or PYY. In the case of template I the epsilon amino groups of lysine may be derivatized with a group facilitating attachment of peptides. For example, as shown in FIG. 5, the epsilon amino groups may be reacted with glyoxylic acid 1,1-diethylacetalsuccinimide ester to form the diethylacetal derivative. After hydrolysis, the resulting aldehyde functions may then be reacted with linear NPY or PYY derived peptides to form a covalent oxime bond. Other covalent bonds that may be formed are shown in FIG. 3 and include hydrazones, amides, thioethers, thioesters, thiazolidines and oxazolidines. A complete description of reactions and the purification of reaction products may be found in the Ernest references cited above as well as in Example 1 below.

B. Synthesis of NPY Linear Peptides

Any method can be used for synthesizing the linear peptides to be attached to templates. Typically peptides have been made using solid phase synthesis techniques (Stewart, et al., *Solid Phase Peptide Synthesis,* 2nd ed., (1984); Fields, et al., Int. *J. Peptide Protein Res.* 35:161–214 (1990)), or by fragment condensation involving the coupling of peptide segments in solution (Lloyd-Williams, et al., Int. *J. Peptides Protein Res.* 37:58–60 (1990); Ernest, et al., *Tetrahedron Lett.* 31:4015–4018 (1990)). Although solid phase synthesis has been optimized so that proteins of about 100 amino acids in length can be made, the accumulation of side products over many coupling steps may render the purification of the target product both laborious and time consuming. Condensation strategies have the advantage that synthesis and purification of peptide segments up to about 30 residues in length is straightforward but they are limited by the poor solubility of fully protected peptide segments in aqueous solution and the tendency of alpha-carboxy-activated peptides to racemize. Many of the difficulties associated with these synthesis methods can be circumvented by using recently developed chemoselective ligation methods (Rose, et al., *Bioconj. Chem.* 7:552–556 (1996); Liu, et al., *J. Am. Chem. Soc.* 116:4149–4153 (1994); Dawson, et al., *J. Am. Chem. Soc.* 115:7263–7266 (1993); Kemp, et al., *J. Org. Chem.* 58:2216–2222 (1993)). These methods allow for the condensation of completely unprotected peptide fragments in aqueous medium (FIG. 3).

In choosing appropriate linear peptides for attachment to templates, the structure of NPY or PYY should serve as a guide. C-terminal residues 25–36 must be present in the linear peptide but longer segments, up to and including the full NPY or PYY sequences, may be used. In addition, conservative amino acid substitutions may be introduced into the sequence. For example, it is expected that a hydrophobic residue in the NPY sequence may generally be substituted with another hydrophobic amino acid without substantially affecting activity. In order to determine whether a particular substitution is acceptable, a linear peptide-template compound may be tested for its ability to bind to NPY receptors and activate cAMP using the procedures described below in Examples 3 and 4.

C. Formation of TASP Agonists

The preferred method for attaching linear peptides to templates is by means of the chemoselective ligation procedures described above. In particular, peptide blocks and templates exhibiting chemoselective addressable functional groups (e.g., aminooxy and aldehyde groups) are prepared by standard methods and, after cleavage of side chain protecting groups, these are reacted to produce bioactive TASP molecules. For example, fragments derived from NPY of variable chain length and sequence (e.g., NPY 2-36, NPY 21-36, NPY 25-36) can be selectively attached to templates according to the strategy outlined in FIG. 5. Similar strategies have been effectively employed for producing a variety of other TASP molecules (see e.g., Grouzmann, et al., *Eur. J. Biochem.* 234:4449 (1995); Tuchscherer, et al., *Protein Sci.* 1:1377–1386 (1992); Futaki, et al., *Tetrahedron Lett.* 38:6237–6240 (1997); Grove, et al., *J. Am. Chem. Soc.* 115:1100–1115 (1993)). Additional guidance concerning appropriate methods that can be employed are set forth in Example 1 using TASP-V as a model.

Once appropriate TASP compounds have been formed, they may be purified using standard procedures in peptide chemistry. One procedure that has been found effective is to purify compounds by reverse-phase HPLC using linear gradients of acetonitrile (see Example 1).

D. Testing of Compounds for Activity

The compounds synthesized by the methods described above may be assayed to determine the extent to which they mimic the effects of NPY or PYY. Radioreceptor binding assays such as those described in Example 3 may be employed to determine whether the compound selectively binds to the Y1 or Y2 receptor. This is accomplished by using cell lines that exclusively produce either Y2 (LN319 cells) or Y1 (SK-N-MC cells). Cyclic AMP assays may be performed in conjunction with binding assays in order to determine whether compounds interacting with receptors are acting as agonists or antagonists of NPY.

Alternatively, any biological assay that has been employed to demonstrate a measurable effect of NPY or PYY may be used in screening TASP compounds for activity. For example, the effect of compounds on rhinitis and bronchospasm may be determined directly using procedures such as those set forth in Example 6.

II. Therapeutic Methods Employing NPY, PYY or Their Agonists

TASP compounds synthesized by the methods described above may be used in treating any disease or condition that responds to NPY or PYY. Because agonists in which linear peptides having less than the full length NPY or PYY sequence interact preferentially with the Y2 receptor, it is expected that these compounds will produce therapeutically desirable effects with fewer undesired side effects. In the case of bronchial diseases and conditions, either agonists, NPY or PYY may be administered for the purpose of reducing airway resistance.

The total daily dosage of agonist, NPY or PYY administered to a patient should be at least the amount required to minimize, reduce or eliminate one or more of the symptoms associated with the disease or condition treated. For example, in the case of rhinitis, sufficient drug should be administered to reduce rhinorrhea and/or alter airway resistance. Ordinarily, a unit dose should contain between 1 and 100 $\mu$g of active agent with the optimal daily dose being determined by methods well known in the art. Dosages may be provided either in a single or multiple daily regimen.

The present invention is not limited to any particular dosage form or route of administration. Although inhalation will generally be most convenient and is preferred in the treatment of rhinitis and bronchial conditions, parenteral, transdermal, sublingual, peroral, nasal, rectal, vaginal, auricular, implantable or other routes of administration may be used as well. Therapeutic agents may be administered in a substantially purified form or as part of a pharmaceutical composition containing one or more excipients, flavoring agents, or other active ingredients. Preparations may be solid or liquid or take any of the pharmaceutical forms presently used in human medicine, e.g., tablets, powders, solutions, creams, ointments, suspensions, gel capsules, granules, suppositories, transdermal compositions or injectable preparations.

The active agents may be incorporated into dosage forms in conjunction with the vehicles that are commonly employed in pharmaceutical preparations, e.g., talc, gum arabic, lactose, starch, magnesium stearate, cocoa butter, aqueous or non-aqueous solvents, oils, paraffin derivatives, glycols, etc. Methods for preparing appropriate formulations are well known in the art (see, e.g., *Remington's Pharmaceutical Sciences*, 16th ed., A. Oslo. ed., Easton Pa. (1980)).

In order to determine the effect of an administered composition on a particular disease or condition, patients should be evaluated on a regular basis over an extended period of time. In some cases, it may take several weeks for the full therapeutic effect of a treatment to become apparent. In other cases, e.g., in the treatment of bronchitis, asthma, and rhinitis, agonists such as TASP-V should produce relief within an hour after administration. Since agonists specific for the Y2 receptor should not produce a rebound effect on airway resistance, these may be administered repeatedly by the patient as desired. The preferred route for these conditions is by inhalation and, as indicated above, each unit dose administered should contain between about 1 and 100 μg of active agent.

EXAMPLES

A new Y2-receptor agonist, TASP-V (FIG. 5) was synthesized and characterized with respect to its effect on the functional response to subsequent histamine challenge. Studies on the modulation of histamine-evoked bronchial and nasal responses by local pretreatment with TASP-V were performed in pigs and in humans. The results demonstrate that:

1. Intranasal pretreatment with TASP-V reduces nasal obstruction induced by histamine.
2. Intrabronchic pretreatment with TASP-V reduces bronchoconstriction evoked by histamine challenge.

Example 1

Synthesis of the Y2-Receptor Agonist TASP-V

Based on molecular dynamics simulations derived from the crystal structure of avian pancreatic polypeptide, the 3D structure of NPY was proposed to be a polyproline-type II helix for residues 1–8, followed by a β-turn at positions 9–14. An amphipatic α-helical segment 15–32 is stabilized by hydrophobic interactions with the polyproline helix and a C-terminal turn structure is adopted by residues 33–36.

The C-terminal part of NPY is essential for receptor binding and biological activity. It is believed that the N-terminal segment 1–4 stabilizes the C-terminal α-helical structure 25–36. The antiparallel PP-fold is of structural importance for the receptor binding of NPY, and its main function is to present the combined C- and N-terminal segments of the molecule to the receptor. As the tetrapeptide NPY33-36per se does not bind to the receptor, it must be assumed that factors like conformational stabilization by N-terminal extension are of particular importance.

The preparation of the cyclic template (I in FIG. 5) has been described previously (Ernest, et al., *Tetrahedron Lett.,* 31:4011–4014 (1990); Ernest, et al., *Helv. Chim. Acta* 76:1539–1563 (1993)). The synthesis of the fully protected neuropeptide Y analogue, NPY21-36 amide (IV in FIG. 5) was performed on Rink amide resin using an Fmoc strategy (Fields, et al., Int. *J. Peptide Protein Res.* 35:161–214 (1990)). All amino acids were used as $N^{\alpha}$-protected derivatives. Side-chain protecting groups were Tyr(t-Bu), Arg (Pmc), Gln (Trt), Thr(t-Bu), Asn(Trt) and Ser(t-Bu). Peptides were constructed semi-automatically according to the published cycle (Akaji, et al., *Chem. Pharm. Bull* 37:2661–2664 (1989)) consisting of (i) a 20 min deprotection of Fmoc with 25% piperidine/DMF (N,N-dimethylformamide) and (ii) a 45 min coupling of the Fmoc amino acid derivatives (1.5 equiv.) by the aid of PyBOP (benzotriazol-1-yl-oxy-tris(pyrrolidino)-phosphonium hexafluorophosphate) (1.7 equiv.) and DIEA (N,N-diisopropylethylamine) (3.5 equiv.) in DMF (N,N-dimethylformamide). The completeness of each coupling was confirmed by the Kaiser test (Kaiser, et al., *Anal. Biochem.* 34:595–598 (1970)). Washing cycles after coupling and deprotection consisted of successive treatments with DMF and dichloromethane. After the peptide sequence was assembled, the functional residue for chemoselective ligation was introduced onto the N-terminus using Boc-aminooxyacetyl-OSu-ester.

For cleavage from the resin and partial deprotection of the fully side-chain protected peptide, the dried resin (800 mg) was treated with 10% trifluoroacetic acid-dichloromethane (5×15 ml). After each treatment, the resin was separated by filtration, and the filtrates were concentrated in vacuo.

In order to completely deprotect the peptide, the residue prepared as described above was retreated for 90 min with trifluoroacetic acid-dichloromethane (9:1, 15 ml) in the presence of triisopropyl-silane/water (1:1, 0.5 ml), and cold diethyl ether was then added to precipitate the product. The crude octadecapeptide amide was collected by centrifugation and lyophilized from water-acetonitrile (1:1) to afford a colorless hygroscopic solid (300 mg).

After lyophilization, the crude product was purified by preparative reverse-phase HPLC on a Vydac 218 TP54 column (5 μm, C18, 25 mm×250 mm) using a linear gradient from 20% to 60% of 0.9% trifluoroacetic acid in acetonitrile over a period of 30 minutes at a flow rate of 18.0 ml/min. The eluate was monitored by measuring the UV absorption at 214 nm, and appropriate fractions were lyophilized. The overall yield was 200 mg (45%). The partial sequence of neuropeptide Y, NPY21-36 (IV in FIG. 5), was characterized by electronspray mass spectrometry and amino acid analysis.

For the effective synthesis of the TASP-V (FIG. 5), chemoselective ligation methods were applied. Oxime bond formation (Nyanguile, et al., *Lett. Peptide Sci.* 1 (1):9–16 (1994); Liu, et al., *J. Am. Chem. Soc.* 116:4149–4153 (1994); Dawson, et al., *J. Am. Chem. Soc.* 115:7263–7266 (1993)) was used to attach the aminooxy acetyl-containing peptide fragments IV to the cyclic peptide template III. contains two lysine residues (acting as attachment sites) and the β-turn mimic, 8-aminomethyl-naphth-2-oic acid (Ernest, et al., *Tetrahedron Lett.,* 31:4011–4014 (1990); Ernest, et al., *Helv. Chim. Acta* 76:1539–1563 (1993)).

The ε-amino groups of lysine were converted to diethylacetal functions by reaction with glyoxylic acid 1,1-diethylacetalsuccinimide ester. The derivatization reaction was monitored by analytical reverse-phase HPLC. Interestingly, two intermediates were observed during the reaction at $t_R$=18.70 min and 18.90 min, which could be identified as the isomeric templates containing one derivatized lysine residue. After 4 h, the template molecule II was purified by preparative reverse-phase HPLC (60% yield) and characterized by electrospray mass spectrometry.

Hydrolysis of the diethylacetal in II was performed by repeated treatment of II (FIG. 5) with 1N HCl—CH₃COOH—H₂O (2:1:2) for 1 h, followed by evaporation under reduced pressure. The reaction is apparently sluggish due to the deactivating effect of the adjacent carbonyl group, and indeed use of trifluoroacetic acid proved to be ineffective. However satisfactory results were obtained with 1N hydrochloric acid. Complete hydrolysis as judged by analytical reverse-phase HPLC was achieved after six treatments to yield III (80%). The byproduct IIa was identified as the analogue carrying an aldehydic function on only one of the lysine residues.

The ligation reaction proceeded as follows. The template di-aldehyde III was dissolved in 1M sodium acetate, and the pH was adjusted to 4.5 with acetic acid. A 1.2-fold excess (with respect to the aldehyde groups) of NPY21-36, (IV), in 1M sodium acetate was added, and the mixture was stirred at room temperature. After 3 h, the condensation reaction was checked by analytical reverse-phase HPLC. Two major products were observed and characterized by ESI-MS. After 15 h, the condensation reaction was complete and the crude product was purified directly by preparative reverse-phase HPLC (45% yield). The isolated TASP-V was characterized by electrospray-mass spectrometry and amino acid analysis.

After each step in the reaction scheme, the product formed was purified before proceeding on to the next step. The α-helix NPY amide (structure IV) and derivatized templates II and III were purified on a Vydac 218TP1022 (5 μm, C18, 22×250 mm) column, using a buffer gradient of B (buffer A: 0.9% trifluoroacetic acid in water; buffer B: 0.9% trifluoroacetic acid in acetonitrile), at 18 ml/min over 30 min, monitoring at 214 nm. The α-helix NPY amide was purified using a gradient of 20–60% buffer B and eluted at 19.8 minutes. Derivatized templates II and III were purified using a gradient of 0–100% buffer B and eluted at 21.9 minutes and 14.8 minutes respectively. TASP-V was purified on the same type of column, using a buffer gradient of 10–50–80% buffer B at 18 ml/min over 40 min, again monitoring at 214 nm. TASP-V eluted at 25.7 min.

Example 2

Conformational Properties

The conformational properties of TASP-V were studied in solution mainly by circular dichroism (CD) spectroscopy under various experimental conditions. In order to detect effects of template attachment on secondary and tertiary structure formation, the corresponding single (not template attached) peptide IV was also studied.

CD spectra were recorded on a Jobin Yvon Dichrograph Mark VI calibrated with D(+)-10-camphorsulfonic acid. All measurements were performed at 295K using quartz cells with a path length of 0.1 cm and each spectrum was the average of three repeated scans between 185 nm to 250 nm, with an integration time of 1s for 0.8 nm steps. The spectra were corrected by substraction of the background solvent spectrum obtained under identical experimental conditions and smoothed for clarity of display. CD intensities are expressed as mean residue ellipticities (deg cm2 dmol-1), calculated by dividing the total molar ellipticities by the number of amino acids in the peptide.

The CD curve of TASP-V displays the typical features of peptides in an α-helical conformation, i.e., strong negative Cotton effects at 222 nm ($\theta_M$=31000 deg cm2 dmol-1) and 210 nm ($\theta_M$=34000 deg cm2 dmol-1), a zero-crossover at 202 nm, and a strong positive Cotton effect at 194 nm. While the single helical peptide IV exhibits weak helicity in TFE (<30%), the attachment of IV to the cyclic template III results in a dramatic increase in secondary structure content (>80%), indicating a strong secondary structure inducing effect of the template.

Example 3

Selectivity of TASP-V for the NPY Y2 Receptor

A. Methods

Cell Culture

SK-N-MC cells that exclusively express the NPY Y1 receptor, were derived from a human neuroblastoma and were cultured according to the American Type cell culture recommendations (Rockville, USA). LN319 cells that express exclusively the NPY Y2 receptor were obtained from a human glioblastoma and grown in Dulbecco's modified Eagle's medium supplemented with 5% fetal calf serum, glutamine, 100 IU of penicillin, and 100 μg/ml of streptomycin in a 5% $CO_2$/95% air incubator at 37° C. Tissue culture media were purchased from Life Technologies (Basel, Switzerland) and fetal calf serum was obtained from Seromed (Berlin, Germany). 70% confluent cells were washed with PBS and harvested using 0.15% Trypsin containing 0.4 mM EDTA. Cells were further diluted ⅓ and plated onto either 60 mm cell culture dishes (Nunc, Denmark) or 12-mm glass coverslips (Huber and Co, AG, Reinach, Switzerland). Media were changed every 3 days.

Y1 Radioreceptor Binding Assay

Binding of iodinated NPY (Amersham, Buckingamshire, UK, 74 Tbq/mmol) was performed by incubation at 37° C. for 1 hour in Eagle's minimum essential medium containing 0.5% BSA, 4 mM $MgCl_2$ and 10 mM Hepes. Various peptide dilutions were incubated with SK-N-MC cells that exclusively express Y1 receptors. Cells were then washed three times with buffer and lysed in 1% Nonidet P40 (Fluka, Neu-Ulm, Germany), 8M urea, 3M acetic acid. Non-specific binding was estimated by carrying out binding reactions in the presence of 1 μM unlabeled NPY. Displacement curves were obtained by incubation of various concentrations of competitive peptides together with a non-saturating dose of iodinated NPY. At the end of the incubation period, cells were washed and lysed. Bound radioactivity was determined by gamma counting. Half maximal inhibition of the binding, obtained with $^{125}$I-NPY, is given as the $IC_{50}$. Each point represents the mean± of at least 4 experiments.

Y2 Radioreceptor Binding Assay

A human glioblastoma cell line, LN319, was used for Y2 binding studies (Greber, et al., *Br. J. Pharmacol.* 113:737–740 (1994)). Prior to performing binding assays, adhered LN319 cells were washed extensively with phosphate buffered saline. The cells were then harvested in 50 mM Hepes, pH7.4, containing 145 mM NaCl, 2.5 mM CaCl2, 1 mM MgCl2, 10 mM glucose, 0.1% (w/v) bovine serum albumin, 0.25 mg/ml bacitracin and 0.025 mg/ml aprotinin. After centrifugation at 600 g for 15 minutes at a temperature of 4° C., the pellet was resuspended in the harvesting buffer. Binding was performed in 50 mM Tris, pH 7.5, that contained 100 mM NaCl, 4 mM $MnCl_2$, 1 mM EGTA, 0.1% BSA, 0.25 mg/ml bacitracin and PMSF 0.07 mg/ml. Incubation proceeded at room temperature for 45 minutes. Bound radioactivity was determined after separating the unbound fraction by centrifugation.

B. Results

As described above, the SK-N-MC and LN319 cells express Y1 and Y2 receptor subtypes, respectively. For competitive binding studies, in addition to native NPY, peptides were used with differential selectivity for Y1 and Y2. Leu31- and Pro34-substituted NPY has been shown to be a Y1 agonist (Schwartz, et al., *Ann. N.Y. Acad. Sci.* 611:35–47 (1990)), whereas NPY13-36 has been reported to bind preferentially to the Y2 receptor subtype.

Figure 6:
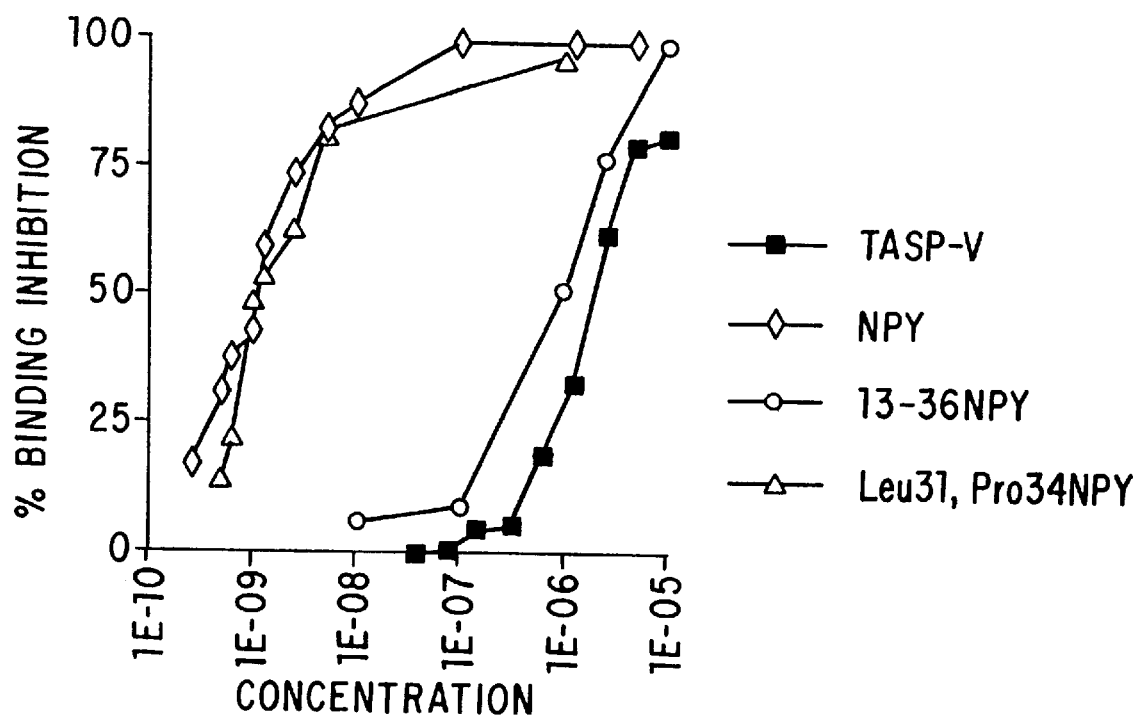
FIG. 6: Representative concentration response curves of the displacement of $^{125}$I-NPY by selective peptides for the Y1 receptor in SK-N-MC cells. Four experiments were performed with each analogue. The percentage inhibition of $^{125}$I-NPY binding to the receptor, which is caused by the increasing concentrations of competitors, is shown on the y axis. High affinity binding to the Y1 receptor on SK-N-MC cells was found for NPY (◇) and Leu31, Pro34 NPY (Δ), whereas poor affinity was observed with NPY13-36(O) and TASP-V (■).
Figure 7:
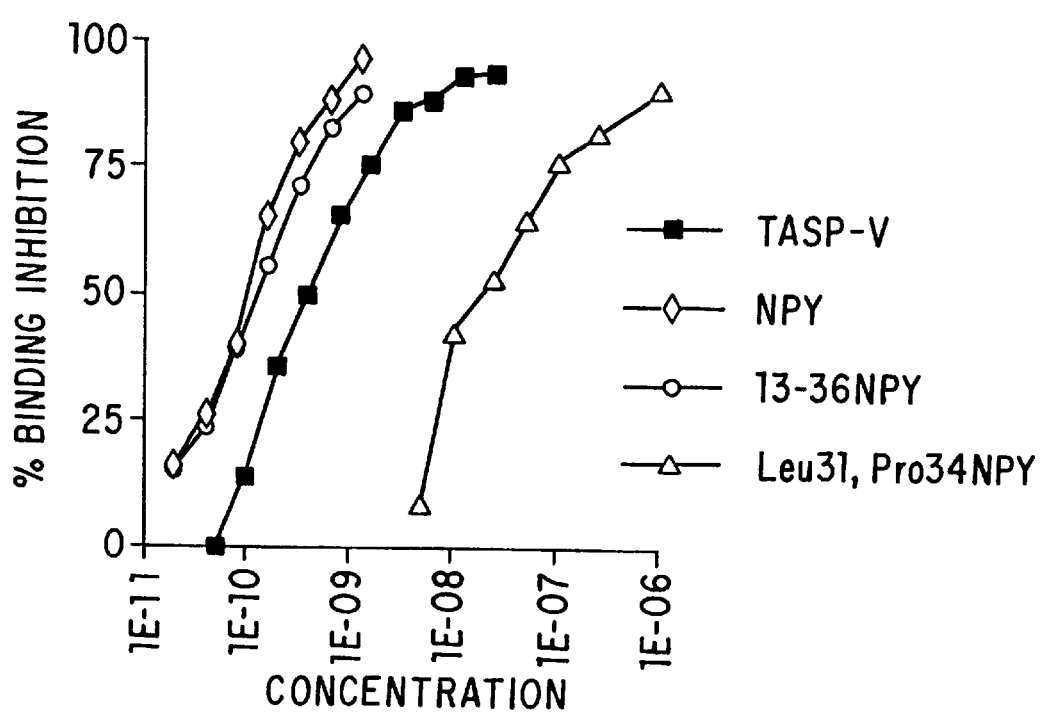
FIG. 7: Representative concentration response curves of the displacement of $^{125}$I-NPY by selective peptides for the Y2 receptor in LN319 cells. Four experiments were performed with each analog. The percentage inhibition of $^{125}$I-NPY binding to the receptor, which is caused by the increasing concentrations of competitors, is shown on the y axis. High affinity binding to the Y2 receptor on LN319 cells was found for NPY (◇), NPY13-36 (O) and TASP-V (■). Leu31, Pro34 NPY (Δ) exhibited poor affinity binding.

FIGS. 6 and 7 depict the results of binding experiments obtained with the two cell lines. SK-N-MC cells (FIG. 6) bind NPY and Leu31, Pro34 NPY equally well as shown by the similar competition displacement curves. In contrast, NPY13-36 binding was 2000 fold less. The template did not bind to SK-N-MC cells ($IC_{50}$>10 μM) and TASP-V shows only a poor affinity for the Y1 receptor ($IC_{50}$=2 μM).

The LN319 cells (FIG. 7) exhibited a comparably high affity for NPY and NPY13-36 with an $IC_{50}$ of 0.085 and 0.126 nM, respectively. In contrast, Leu31, Pro34 NPY bound poorly to the Y2 receptor. The template exhibited no affinity for LN319 cells ($IC_{50}$>10 μM) but good binding to the Y2 receptor was obtained with TASP-V ($IC_{50}$=0.379 nM).

Example 4

Determination of cAMP

Six-well plates, containing confluent LN319 cell cultures, were washed and incubated at 37° C. for 1 hour in Eagle's minimum essential medium containing 0.5% BSA, 4 mM $MgCl_2$, 10 mM Hepes, 100 μM papaverin and 2.5 μM forskolin and one of the peptides to be tested in varying dilutions. Cells were washed once in sodium phosphate buffer (100 mM pH7.5) and lysed with 0.75 ml of 0.1 M HCl. After centrifugation, the supernatant was recovered and lyophilized. cAMP concentration was measured by a RIA using a commercially available kit (Amersham).

It was found that NPY inhibits forskolin-stimulated cAMP accumulation in LN319 cells with an $IC_{50}$ of 2.5 nM and that TASP-V has an $IC_{50}$ of 3.4 nM. These data indicate that TASP-V acts as a fill agonist at the Y2 receptor.

Example 5

Rat In Vivo Assay

A. Methods

Experiments were carried out in adult female Wistar rats weighing 230–280 g and anaesthetised with sodium pentobarbitone (Nembutal, Boehringer-Ingleheim; 60 mg/kg, intraperitoneal). Intravenous supplements of pentobarbitone was given to maintain a surgical plane of anaesthesia. The trachea was cannulated and attached to a positive pressure rodent ventilator (Ugo Basile 6025). The left femoral artery was cannulated for continuous recording of arterial blood pressure via a Gould-Statham physiological pressure transducer (P23XL) which was connected to one channel of a pen recorder (Graphtec WR7400). Temperature was continuously monitored via a rectal probe (Digitron Model 1808) and kept in the range 34±1° C. An electrocardiogram was recorded through sub-cutaneous needle electrodes and displayed on a storage oscilloscope. The electrocardiogram was used to obtain a beat-by-beat pulse interval (PI- time between successive heart beats) after processing with Neurolog modules (Digitimer, England NL200,304,600). Triggering was checked with a counter. PI was preferred to heart rate because of the linear relation between PI and frequency of vagal stimulation.

Both vagus nerves were cut high in the neck. This was done to eliminate vagally mediated reflex effects on the heart which occur when blood pressure is increased by NPY. The cardiac end of the right vagus nerve was stimulated every 30 seconds with a 6 second train of supramaximal stimuli (2 Hz, 1 ms, 7v) using an isolated, square wave stimulator (Grass Instruments SD9). The frequency was chosen to increase pulse interval by approximately 100 ms, a submaximal effect of this variable. The left femoral vein was cannulated for administration of NPY (Novabiochem, Human NPY 1-36) and TASP-V (diluted in saline), as well as further doses of anaesthetic. To indicate prejunctional activity two parameters were measured; the maximum percent inhibition of the increase in pulse interval (ΔPI) evoked by stimulation of the vagus nerve following injection of the peptide and the time to half recovery of this effect (T50). For an indication of postjunctional activity, the pressor action was measured as the peak response following injection of the peptide (ΔBP) and the duration of this response (BP duration).

B. Results

Figure 9:
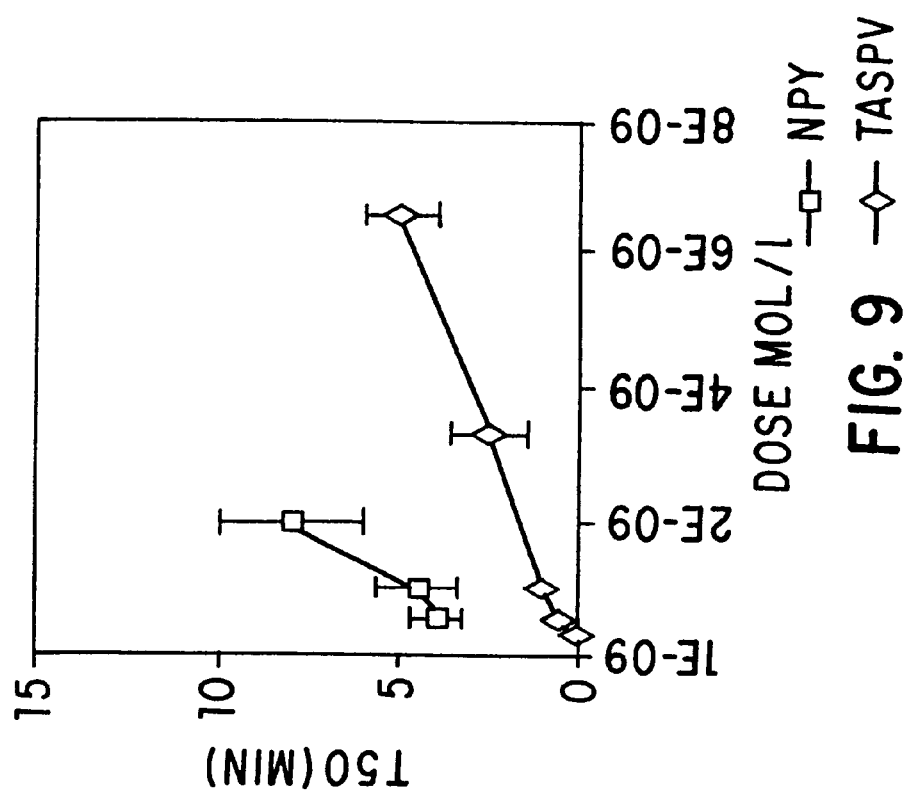
FIG. 9: Prejunctional activity of TASP-V measured in rat and expressed as the time to half recovery of this effect (T50).
Figure 8:
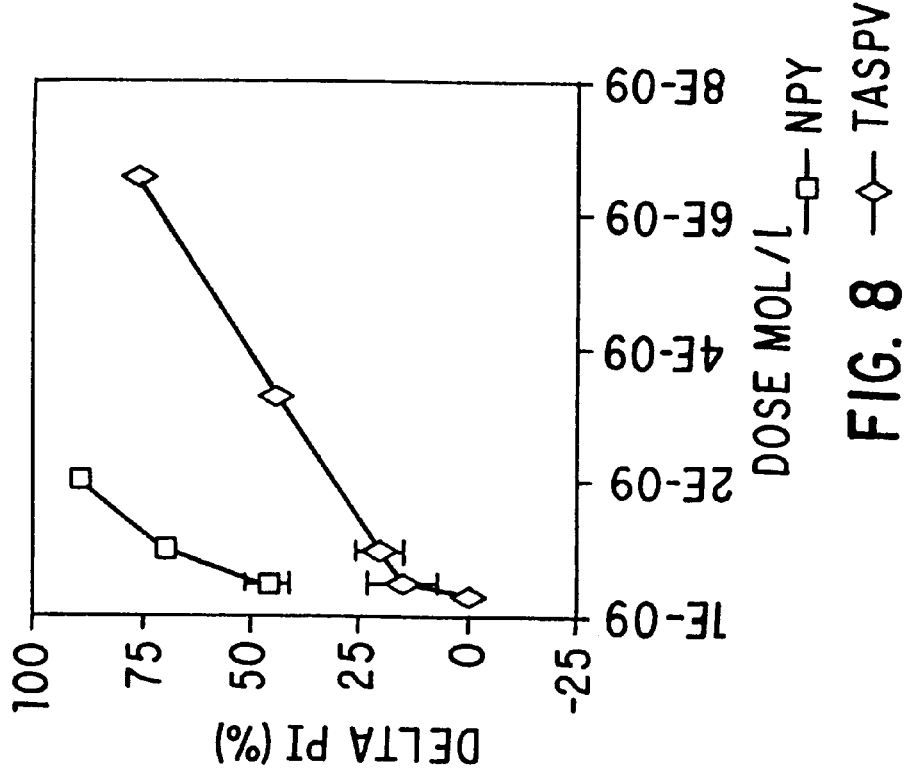
FIG. 8: Prejunctional activity of TASP-V measured in rat and expressed as the maximum percent inhibition of the increase in pulse interval (ΔPI) evoked by stimulation of the vagus nerve following injection of TASP-V.

As shown in FIGS. 8 and 9, TASP-V was found to have no postjunctional activity since the pressor action measured as the peak response following injection of the peptide (ΔBP) and the duration of this response (BP duration) was only significant with NPY that activates both the NPY Y1 and Y2 receptors. In contrast, TASP-V exhibits a prejunctional activity similar to that observed with NPY as depicted in FIGS. 10 and 11 by the ΔPI and the T50.

Example 6

Effect of TASP-V on Histamine-Induced Rhinitis and Bronchospasm in Minipigs

A. Methods

Animals

Experiments were performed on 16 domestic pigs of both sexes (body weight 20–30 kg). The animals were premedicated with atropine (0.05 mg/kg) and ketamine (Ketalar, ParkeDavis, USA, 20 mg/kg i.m.) and anaesthetized with thiopentone (5 mg/kg i.v.). A tracheostomy was performed and artificial ventilation was started using a volume regulated ventilator (type Siemens 900). During surgery, continuous i.v. infusion of Ringer's solution, thiopentone (15 mg/kg/h) and pancuronium bromide (0.25 mg/kg/h) was performed.

Surgical Procedure

Catheters were placed in the femoral artery for systemic blood pressure and heart rate monitoring and in the femoral vein for thiopentone and fluid administration (300 ml/h). Surgical preparation of the maxillary artery similar to that described in a previous report (Lacroix, et al., *Acta Physiol. Scand.* 132:83–90 (1988)) was performed. Nasal arterial blood flow was monitored with a Transonic flow probe (RB 143) placed around the sphenopalatine artery and connected to a T 202 ultrasonic blood flowmeter (Transonic System Inc., Ithaca, N.Y., USA).

Administration of Histamine

In early experiments (n=7), tachyphylaxis to histamine was investigated by 3 successive nasal and bronchial histamine challenges at 30 minute intervals. Histamine (5 mg in 1 ml of saline, Sigma, St. Louis, USA) was sprayed with a hand held nebulizer in the left nostril under controlled conditions, and repeated 15 minutes after intranasal spray of TASP-V (85 μg in 1 ml of NaCl 0.9%).

In other experiments, histamine (10 mg in 3 ml of saline) was aerosolized for 3 minutes in the trachea with a nebulisator (Acorn 2, ref. 124010, Marquest Medical, Col., USA) fixed to the inspiratory division of the ventilation tube and supplemented by oxygen (4 l/min) under controlled conditions. This procedure was repeated 15 minutes after intratracheal nebulization of 200 µg–400 µg of TASP-V in 3 ml of saline.

Measurements of Parameters

In all animals, the bronchial and nasal vascular responses to histamine challenge were recorded under controlled conditions before and after pretreatment with TASP-V. By use of a six channel pen trace recorder (Gould Electronics) the following parameters were recorded simultaneously:

1. Heart rate and systemic arterial blood pressure using the femoral artery catheter connected to a pressure transducer.
2. Pulmonary airway resistance and compliance. Airway pressure was measured from a catheter positioned at the tip of the endotracheal tube. Transpulmonary pressure was determined by a differential pressure transducer (Hewlett-Packard 267B) taking the difference between tracheal and oesophagus pressure. Tidal volume was determined by integration of the respiratory flow signal measured with a pneumotachograph (Gould Godard, model 17212) by means of a heated Fleisch flow transducer #2 connected to the endotracheal tube. Transpulmonary pressure, tidal volume and flow were continuously recorded on a 4-channel recorder (Hewlett-Packard, 7754 GB). Total airflow resistance across the lungs (raw) was determined by dividing the difference in transpulmonary pressure by inspiratory plus expiratory flow at mid-tidal volume. Dynamic pulmonary compliance (Cdyn) was obtained by dividing tidal volume by the difference in transpulmonary pressure at points of zero flow. Respiratory parameters were averaged for five successive tidal volumes.
3. Sphenopalatine arterial blood flow using an Ultrasonic flow meter probe (see above).

B. Results

The initial triple challenge with nasal histamine resulted in a reproducible 10±4% increase of the sphenopalatine blood flow, and a 10±4% decrease in vascular resistance. No tachyphylactic phenomenon could be elicited in the bronchi. There was a reproducible 100±27% increase in airway resistance and 38±10% reduction of dynamic lung compliance. No cardiac effect following the challenge, either by the nasal or bronchial route, was recorded. The intranasal or intrabronchial administration of TASP-V did not induce any change in heart rate or mean arterial blood pressure.

Following pretreatment with TASP-V, the increase in sphenopalatine blood flow after histamine challenge was statistically reduced by 50±5.5%, with a maximum effect after 45 minutes. The reduction of vascular resistance induced by histamine was not significantly modified after TASP-V pretreatment.

Two different doses of TASP-V were tested. After pretreatment with 200 µg, the increase of airway resistance following the histamine challenge was attenuated by 15±10%, with a maximum effect observed after 90 minutes ($p<0.05$). The dynamic lung compliance reduction was also significantly reduced after 45 minutes). A stronger effect was observed when 400 µg dose was used, with an attenuation of 50±45%, and the same kinetics ($p<0.05$).

Example 7

Effect of TASP-V on Histamine-Induced Rhinitis in Healthy Volunteers

Eleven healthy volunteers, 6 males and 5 females, aged from 23 to 48, underwent a daily study designed on a randomized, double blind, cross-over basis. Exclusion criteria included abnormal nasal mucosa; anatomical nasal obstruction (such as obstructing nasal polyps); gross anatomical nasal deformity (such as markedly deviated septum); and use of any nasal treatment, such as vasoconstrictors or corticosteroids, in the preceding 30 days.

Pretreatment

TASP-V (diluted in saline) and the placebo (saline) were prepared before each experiment by a technician not involved in the study. Each patient underwent a local pretreatment with saline or TASP-V (85 µg in a total of 200 µl of NaCl 0.9%). One substance was applied and tested over a period of 2 hours, the other substance being applied and tested over the same period following a break of 3 hours between the 2 tests. In order to minimize the risk of bias produced by the cross-over, the peptide was tested in one nostril while the placebo was used in the contralateral one, with a randomized and double blind allocation.

Stimulation 15 minutes after pretreatment with 85 µg of TASP-V or placebo, intranasal application of histamine (1 mg. in 200 µl of saline, Sigma, St. Louis, USA) was performed in the same nostril.

Measurement of Parameters

The parameters listed below were measured prior to the TASP-V pretreatment (T-30', T-15'), then once 15 minutes after it. Following the histamine challenge, the same parameters were repeatedly measured at 15 minute intervals during 1 hour (T15, 30, 45 and 60). These were as follows:

1. Symptoms: A visual analogue scale, graded from 0 to 5 (where 0 represented the absence of symptom and 5 severe intensity of symptoms) was used to assess the degree of subjective nasal obstruction and rhinorrhea.
2. Nasal secretions and sneezings: Nasal secretions produced during the 15 minutes after the histamine challenge were collected by nose-blowing in a preweighted tissue. The number of sneezes was also recorded.
3. Rhinomanometry: Nasal airway resistance (NAR) was recorded in each nostril by anterior rhinomanometry (Rhinotest MP 441, EVG Elektronic, Vertriebs, Germany). Mean resistance values for each nostril were obtained after 10 normal breaths and were calculated at a pressure of 150 Pa.
4. Acoustic rhinometry: The minimal cross section area (MCSA) of the nasal airways opposed to the respiratory flow was evaluated using an acoustic rhinometer (Rhinoclak, Germany), the patient being seated in an ENT chair with the head fixed on the same position during each MCSA recording.

Statistical analysis

Data are given as means+SEM. Statistical differences in symptom scores, NAR, and nasal secretions were estimated using a paired Student t-test analysis and one-way analysis of variance (ANOVA) followed by a Dunnett comparison.

B. Results

Figure 12A:
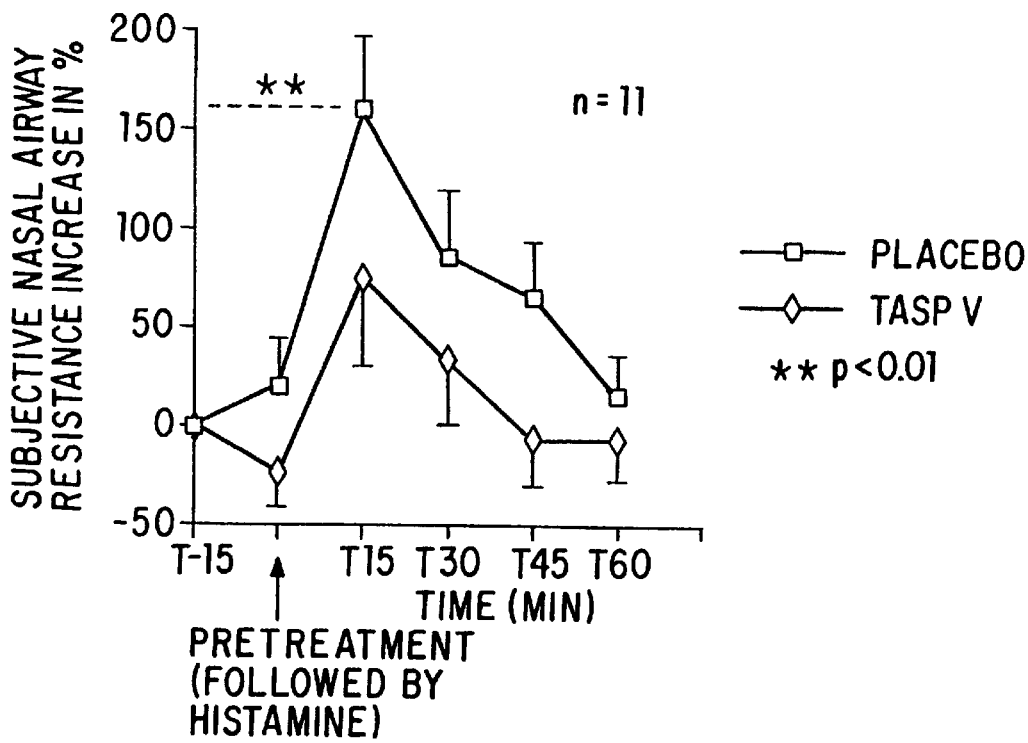
FIG. 12 (panels a and b): Time course variations of subjective (panel a) and objective (panel b) nasal airway resistance (NAR, measured by a visual analogue scale graded from 0 to 5 and anterior rhinomanometry, respectively) in the homolateral nostril following an intranasal application of histamine (1 mg in 200 μg of saline) and after pretreatment with TASP-V or placebo (saline spray). Pretreatment with TASP-V significantly limits the subjective and objective increase of nasal airway resistance. Maximum effect is obtained 15 minutes after the pretreatment (n=11). *p<0.05, **p<0.01 (one-way analysis of variance ANOVA).
Figure 12B:
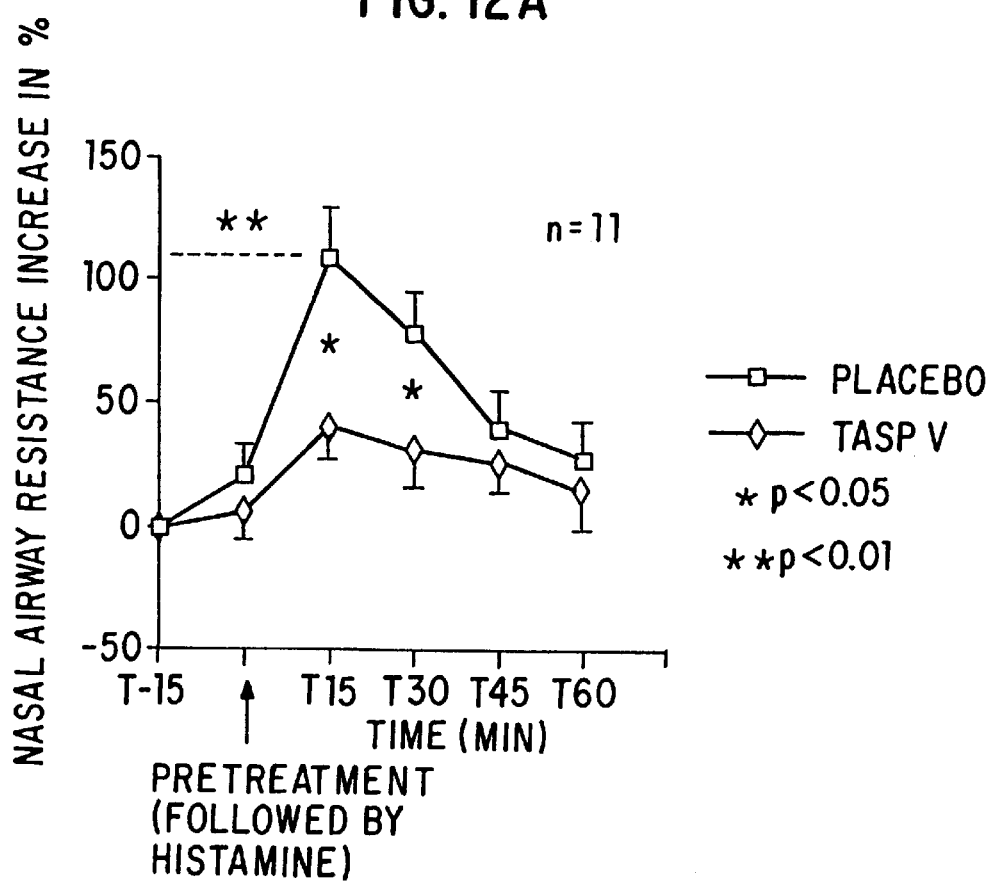
Figure 13:
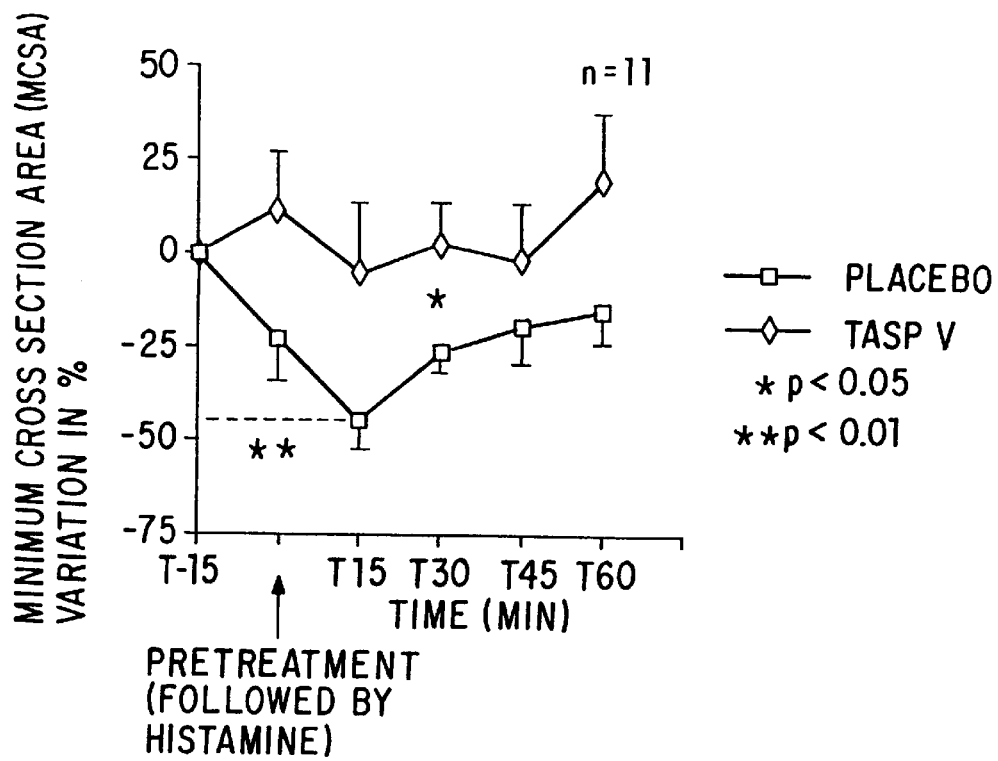
FIG. 13: Time course variations of the minimal cross sectional area (MCSA, measured by acoustic rhinometry) in the homolateral nostril following an intranasal application of histamine (1 mg in 200 μg of saline) and after pretreatment with TASP-V or placebo (saline spray). Pretreatment with TASP-V significantly limits the decrease in cross sectional surface following the histamine challenge. Maximum effect is obtained 15 minutes after the pretreatment (n=11). *p<0.05, **p<0.01 (one-way analysis of variance ANOVA).

The intanaal spray of TASP-V did not produce any subjective local irritation, sneezing or increase in rhinorrhea. No significant modification of the subjective nasal resistance was recorded (FIG. 12a). Rhinomanometry and acoustic rhinometry did not demonstrate any significant change of nasal airway resistance or MCSA (FIGS. 12b and 13).

In all patients, histamine challenge following placebo induced rapid onset of itching, sneezing, rhinorrhea and objective and subjective nasal obstruction (FIG. 12–15). The maximum obstructive effect was observed 15 minutes following the histamine challenge. No statistical residual effect remained after 60 minutes.

Figure 14:
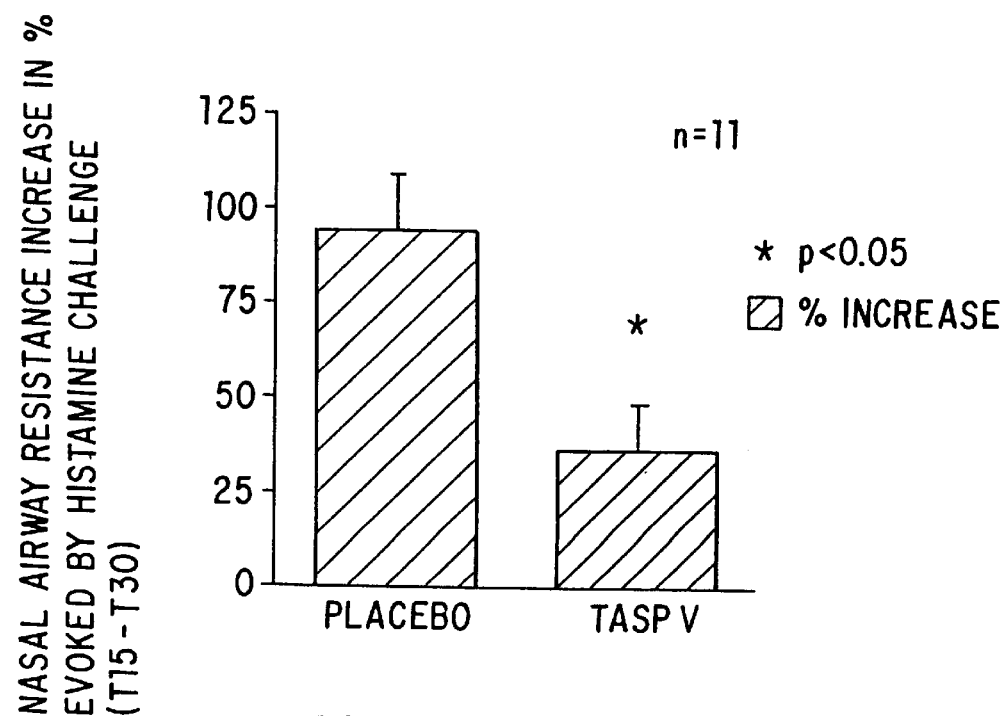
FIG. 14: Effect of an intranasal spray of histamine (1 mg in 200 μg of saline) on the homolateral nasal airway resistance (NAR) measured by anterior rhinomanometry (n=11) and following pretreatment with placebo or TASP-V. Pretreatment with TASP-V significantly limits the increase of nasal airway resistance (n=11). *p<0.05 (one-way analysis of variance ANOVA).
Figure 15:
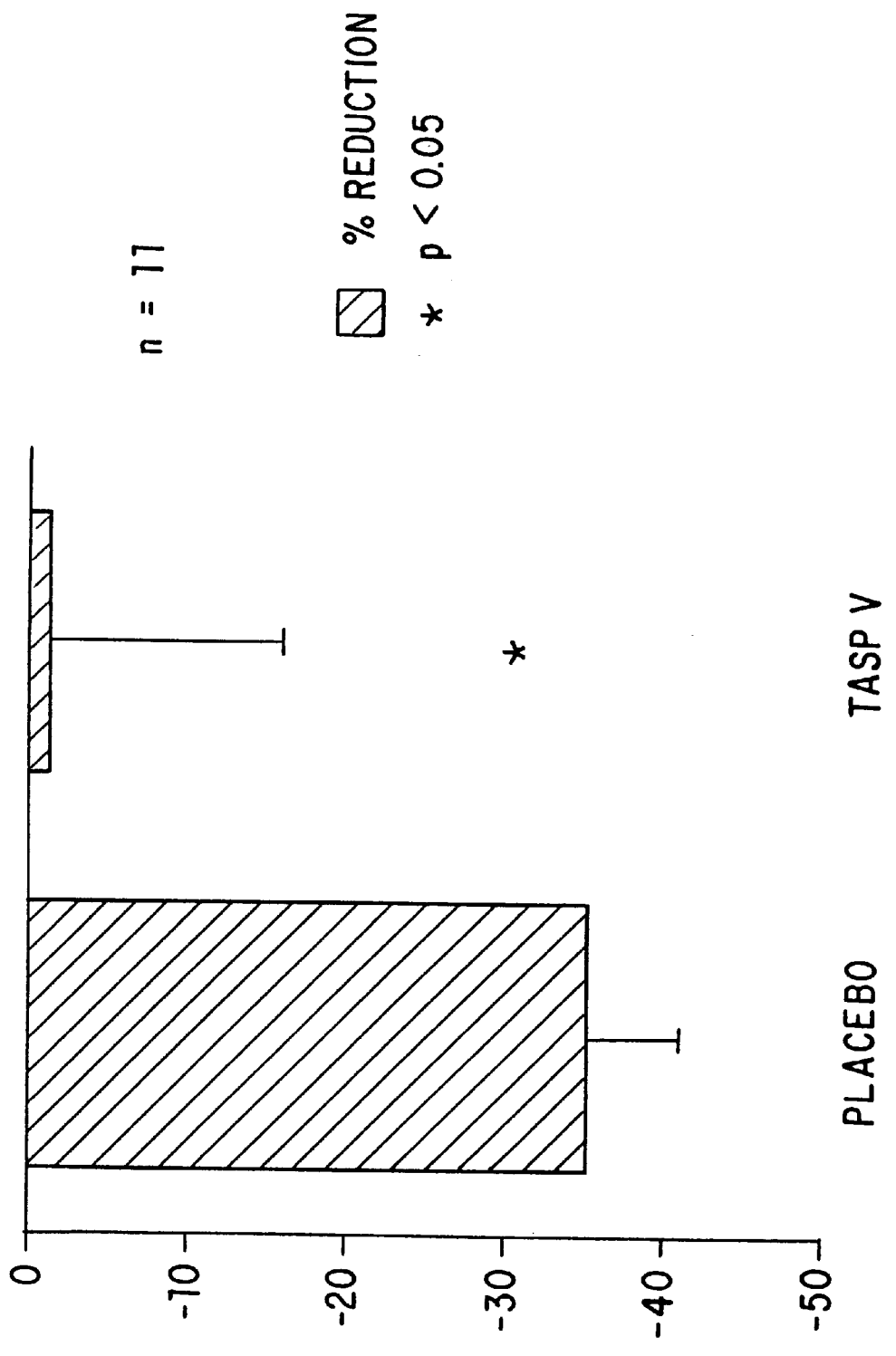
FIG. 15: Effects of an intranasal spray of histamine (1 mg in 200 μg of saline) on the homolateral minimal cross sectional area (MCSA) measured by acoustic rhinometry and following pretreatment with placebo or TASP-V. Pretreatment with TASP-V significantly limits the decrease of the nasal cross section surface (n=11). *p<0.05 (one-way analysis of variance ANOVA).

Pretreatment with TASP-V did not significantly reduce subjective or objective rhinorrhea or the number of sneezes following histamine challenge. However, the increase of nasal airway resistance induced by the allergen challenge, expressed in percent of the initial value (mean of T01 and T02), was significantly reduced by the TASP-V pretreatment (FIGS. 12b, 14). The maximum effect was observed after 15 and 30 minutes. Similarly, the histamine-induced reduction of MCSA was significantly attenuated by TASP-V pretreatment with a maximum effect at 15 and 30 minutes (FIGS. 13, 15). Though non-significant, the subjective homolateral nasal obstruction produced by the histamine challenge appeared to be reduced after TASP-V pretreatment, again with a maximum effect after 15 and 30 minutes (FIG. 12a). None of the patients reported any side effects during the 24 hours following the experiment.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of reducing airway resistance in a patient suffering from a bronchial disease or condition, comprising administering a therapeutically effective dose of a NPY or PPY agonist to said patient, wherein said NPY or PPY agonist comprises:

a) a template comprising a cyclized peptide 3 to 10 amino acid in length, wherein at least two residues in said cyclized peptide are joined by a naphthyl ring at the 2 and 8 position of said naphthyl ring; and b) at least one linear peptide between 12 and 37 amino acids in length covalently bound to said template, wherein said linear peptide has a C-terminal sequence selected from the group consisting of: RHYINLITRQRY, (SEQ ID NO:3); and RHYLNLVTRQRY (SEQ ID NO:4); and wherein the C-terminal tyrosine of said linear peptide is amidated.

2. The method of claim 1, wherein said template has the structure:

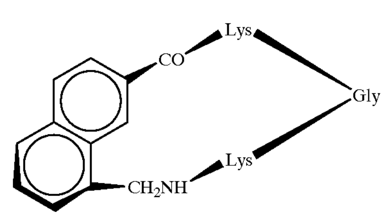

and wherein said linear peptide is attached to said template at either or both of the lysine residues.

3. The method of claim 2, wherein if the C-terminal sequence is SED ID NO:3, said C-terminal sequence is preceded at the N terminal end by between 1 and 24 residues of amino acids 1–24 of NPY, said sequence being: YPSKPDNPGEDAPAEDMARYYSAL (SEQ ID NO:5).

4. The method of claim 3, wherein said linear peptide has the sequence: YSALRHYINLITRQRY (SEQ ID NO:6).

5. The method of claim 3, wherein said linear peptide further comprises an aminooxy acetylated glycine at its N terminus.

6. The agonist of claim 3, wherein said linear peptide is bound to said template by an oxime bond.

7. The method of claim 2, wherein if the C-terminal sequence is SEO ID NO:4, said C-terminal sequence is preceded at the N terminal end by between 1 and 24 residues of amino acids 1–24 of PYY, said sequence being: YPIK-PEAPGEDASPEELNRYYASL (SEQ ID NO:7).

8. The method of claim 7, wherein said linear peptide has the sequence: YASLRHYLNLVTRQRY (SEQ ID NO:8).

9. The method of claim 8, wherein said linear peptide further comprises an aminooxy acteylated glycine at its N terminus.

10. The method of claim 8, wherein said linear peptide is bound to said template by an oxime bond.

11. The method of claim 1, wherein said NPY or PPY agonist is in a pharmaceutical composition administered by inhalation and said NPY or PPY agonist is administered at a dose of between 1 and 100 μg.

12. The method of claim 1, wherein said bronchial disease or condition is asthma.

13. The method of claim 1, wherein said bronchial disease or condition is bronchitis.

14. The method of claim 1, wherein said bronchial disease or condition is rhinitis.

15. The method of claim 1, wherein said agonist is either TASP-V or TASP-V2.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 97 amino acids
      (B) TYPE: amino acid
      (C) STRANDEDNESS: Not Relevant
      (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO: 1:

```
Met Leu Gly Asn Lys Arg Leu Gly Leu Ser Gly Leu Thr Leu Ala Leu
1               5                   10                  15

Ser Leu Leu Val Cys Leu Gly Ala Leu Ala Glu Ala Tyr Pro Ser Lys
            20                  25                  30

Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
    50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp
```

(2) INFORMATION FOR SEQ ID NO: 2:

(i) SEQUENCE CHARACTERISTICS:
      (A) LENGTH: 36 amino acids
      (B) TYPE: amino acid
      (C) STRANDEDNESS: Not Relevant
      (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO: 2:

Tyr Pro Ile Lys Pro Glu Ala Pro Gly Glu Asp Ala Ser Pro Glu Glu

```
       1               5              10              15
Leu Asn Arg Tyr Tyr Ala Ser Leu Arg His Tyr Leu Asn Leu Val Thr
            20                  25                  30
Arg Gln Arg Tyr
        35
```

(2) INFORMATION FOR SEQ ID NO: 3:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO: 3:

```
Arg His Tyr Ile Asn Leu Ile Thr Arg Gln Arg Tyr
1               5                  10
```

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO: 4:

```
Arg His Tyr Leu Asn Leu Val Thr Arg Gln Arg Tyr
1               5                  10
```

(2) INFORMATION FOR SEQ ID NO: 5:

(i) SEQUENCE CHARACTERISTICS:
        (A) LENGTH: 24 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO: 5:

```
Tyr Pro Ser Lys Pro Asp Asn Pro Gly Glu Asp Ala Pro Ala Glu Asp
1               5                  10                  15
Met Ala Arg Tyr Tyr Ser Ala Leu
            20
```

(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant -continued

```
    (ii) MOLECULE TYPE: peptide (iii) HYPOTHETICAL: NO (iv) ANTI-SENSE: NO (xi) SEQUENCE DESCRIPTION: SEQ ID NO: 6:

Tyr Ser Ala Leu Arg His Tyr Ile Asn Leu Ile Thr Arg Gln Arg Tyr
1               5                   10                  15

(2) INFORMATION FOR SEQ ID NO: 7:

(i) SEQUENCE CHARACTERISTICS:
          (A) LENGTH: 24 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO: 7:

Tyr Pro Ile Lys Pro Glu Ala Pro Gly Glu Asp Ala Ser Pro Glu Glu
1               5                   10                  15

Leu Asn Arg Tyr Tyr Ala Ser Leu
            20

(2) INFORMATION FOR SEQ ID NO: 8:

(i) SEQUENCE CHARACTERISTICS:
          (A) LENGTH: 16 amino acids
          (B) TYPE: amino acid
          (C) STRANDEDNESS: Not Relevant
          (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO: 8:

Tyr Ala Ser Leu Arg His Tyr Leu Asn Leu Val Thr Arg Gln Arg Tyr
1               5                   10                  15
```